(12) United States Patent
Nandra et al.

(10) Patent No.: US 10,786,673 B2
(45) Date of Patent: Sep. 29, 2020

(54) NEUROMODULATION SYSTEMS AND METHODS OF USING SAME

(71) Applicant: California Institute of Technology, Pasadena, CA (US)

(72) Inventors: Mandheerej Nandra, Pasadena, CA (US); Yu-Chong Tai, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/713,456

(22) Filed: Sep. 22, 2017

(65) Prior Publication Data

US 2018/0185648 A1     Jul. 5, 2018

Related U.S. Application Data

(63) Continuation of application No. 14/596,118, filed on Jan. 13, 2015, now abandoned.

(Continued)

(51) Int. Cl.
*A61N 1/36*     (2006.01)
*A61B 5/0488*     (2006.01)
(Continued)

(52) U.S. Cl.
CPC ........ *A61N 1/36103* (2013.01); *A61B 5/0031* (2013.01); *A61B 5/0488* (2013.01); *A61B 5/4836* (2013.01); *A61N 1/0553* (2013.01); *A61N 1/36003* (2013.01); *A61N 1/36067* (2013.01); *A61N 1/36139* (2013.01); *A61N 1/36185* (2013.01); *A61B 2562/0219* (2013.01);

(Continued)

(58) Field of Classification Search
None
See application file for complete search history.

(56) References Cited

U.S. PATENT DOCUMENTS 3,543,761 A     12/1970   Bradley
3,662,758 A     5/1972   Glover
(Continued)

FOREIGN PATENT DOCUMENTS

JP     2002-200178     7/2002
JP     2008-067917 A     3/2008
(Continued)

OTHER PUBLICATIONS

Office Action for Canadian Patent Application No. 2,824,782 dated Nov. 29, 2017.

(Continued)

*Primary Examiner* — Ankit D Tejani
(74) *Attorney, Agent, or Firm* — K&L Gates LLP

(57) ABSTRACT

Neuromodulation systems are described. An example neuromodulation system includes a controller wirelessly communicatively coupled to a host computer, a signal generator communicatively coupled to the controller, and a plurality of electrodes communicatively coupled to the signal generator. The controller, in conjunction with the signal generator and the at least one electrode are configured to deliver a stimulation to a mammal based on an instruction received from the host computer. The stimulation is configured to induce voluntary movement or restore function in the mammal.

20 Claims, 9 Drawing Sheets

Related U.S. Application Data

(60) Provisional application No. 61/926,457, filed on Jan. 13, 2014.

(51) Int. Cl.
  *A61B 5/00* (2006.01)
  *A61N 1/05* (2006.01)
  *A61N 1/378* (2006.01)

(52) U.S. Cl.
  CPC .............. *A61B 2562/0247* (2013.01); *A61B 2562/0271* (2013.01); *A61N 1/0558* (2013.01); *A61N 1/3787* (2013.01)

(56) References Cited

U.S. PATENT DOCUMENTS

| | | |
|---|---|---|
| 3,724,467 A | 4/1973 | Avery et al. |
| 4,044,774 A | 8/1977 | Corbin et al. |
| 4,102,344 A | 6/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,800,898 A | 1/1989 | Hess et al. |
| 4,934,368 A | 6/1990 | Lynch |
| 5,002,053 A | 3/1991 | Garcia-Rill et al. |
| 5,031,618 A | 7/1991 | Mullett |
| 5,081,989 A | 1/1992 | Graupe |
| 5,121,754 A | 6/1992 | Mullett |
| 5,344,439 A | 9/1994 | Otten |
| 5,354,320 A | 10/1994 | Schaldach |
| 5,374,285 A | 12/1994 | Vaiani et al. |
| 5,417,719 A | 5/1995 | Hull et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,470,213 B1 | 10/2002 | Alley |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen |
| 6,871,099 B1 | 3/2005 | Whitehurst et al. |
| 6,892,098 B2 | 5/2005 | Ayal |
| 6,895,280 B2 | 5/2005 | Meadows |
| 6,895,283 B2 | 5/2005 | Erickson et al. |
| 6,937,891 B2 | 8/2005 | Leinders |
| 6,950,706 B2 | 9/2005 | Rodriguez |
| 6,975,907 B2 | 12/2005 | Zanakis |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng |
| 7,127,287 B2 | 10/2006 | Duncan |
| 7,127,296 B2 | 10/2006 | Bradley |
| 7,127,297 B2 | 10/2006 | Law et al. |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen |
| 7,239,920 B1 | 7/2007 | Thacker et al. |
| 7,251,529 B2 | 7/2007 | Greenwood-Van |
| 7,252,090 B2 | 8/2007 | Goetz |
| 7,313,440 B2 | 12/2007 | Miesel et al. |
| 7,330,760 B2 | 2/2008 | Heruth et al. |
| 7,337,005 B2 | 2/2008 | Kim |
| 7,377,006 B2 | 2/2008 | Kim |
| 7,340,298 B1 | 3/2008 | Barbut |
| 7,415,309 B2 | 8/2008 | McIntyre |
| 7,463,927 B1 | 12/2008 | Chaouat |
| 7,463,928 B2 | 12/2008 | Lee |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,890,182 B2 | 2/2011 | Parramon et al. |
| 7,949,395 B2 | 5/2011 | Kuzma |
| 7,949,403 B2 | 5/2011 | Palermo |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt |
| 8,155,750 B2 | 4/2012 | Jaax |
| 8,170,660 B2 | 5/2012 | Dacey |
| 8,190,262 B2 | 5/2012 | Gerber |
| 8,195,304 B2 | 6/2012 | Strother et al. |
| 8,239,038 B2 | 8/2012 | Wolf |
| 8,260,436 B2 | 9/2012 | Gerber et al. |
| 8,311,644 B2 | 11/2012 | Moffitt |
| 8,332,029 B2 | 12/2012 | Glukhovsky et al. |
| 8,346,366 B2 | 1/2013 | Arle |
| 8,352,036 B2 | 1/2013 | Dimarco |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishmamur |
| 8,805,542 B2 | 8/2014 | Tai |
| 2002/0055779 A1 | 5/2002 | Andrews |
| 2002/0111661 A1 | 8/2002 | Cross et al. |
| 2003/0032992 A1 | 2/2003 | Thacker |
| 2003/0078633 A1 | 4/2003 | Firlik et al. |
| 2004/0044380 A1 | 3/2004 | Buringa |
| 2004/0122483 A1 | 6/2004 | Nathan et al. |
| 2004/0133248 A1 | 7/2004 | Frei et al. |
| 2004/0138518 A1 | 7/2004 | Rise et al. |
| 2004/0172097 A1 | 9/2004 | Brodard et al. |
| 2004/0181263 A1 | 9/2004 | Blazer et al. |
| 2005/0004622 A1 | 1/2005 | Cullen et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0231186 A1 | 10/2005 | Barrera et al. |
| 2005/0246004 A1 | 11/2005 | Cameron et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0122678 A1 | 6/2006 | Olsen et al. |
| 2006/0142822 A1 | 6/2006 | Tulgar |
| 2006/0149337 A1 | 7/2006 | John |
| 2006/0195153 A1 | 8/2006 | DiUbaldi et al. |

(56) References Cited

U.S. PATENT DOCUMENTS

| | | |
|---|---|---|
| 2006/0239482 A1 | 10/2006 | Hatoum |
| 2006/0241356 A1 | 10/2006 | Flaherty |
| 2007/0016097 A1 | 1/2007 | Farquhar et al. |
| 2007/0049814 A1 | 3/2007 | Muccio |
| 2007/0060954 A1 | 3/2007 | Cameron et al. |
| 2007/0060980 A1 | 3/2007 | Strother et al. |
| 2007/0083240 A1 | 4/2007 | Peterson et al. |
| 2007/0156179 A1 | 7/2007 | S.E. |
| 2007/0179534 A1 | 8/2007 | Firlik et al. |
| 2007/0191709 A1 | 8/2007 | Swanson |
| 2007/0233204 A1 | 10/2007 | Lima et al. |
| 2007/0265691 A1 | 11/2007 | Swanson |
| 2008/0009927 A1 | 1/2008 | Vilims |
| 2008/0046049 A1 | 2/2008 | Skubitz et al. |
| 2008/0051851 A1 | 2/2008 | Lin |
| 2008/0103579 A1 | 5/2008 | Gerber |
| 2008/0140152 A1 | 6/2008 | Imran et al. |
| 2008/0140169 A1 | 6/2008 | Imran |
| 2008/0183224 A1 | 7/2008 | Barolat |
| 2008/0221653 A1 | 9/2008 | Agrawal |
| 2008/0228250 A1 | 9/2008 | Mironer |
| 2008/0234791 A1 | 9/2008 | Arle et al. |
| 2008/0294226 A1 | 11/2008 | Moffitt et al. |
| 2009/0112281 A1 | 4/2009 | Miyazawa et al. |
| 2009/0204173 A1 | 8/2009 | Fang et al. |
| 2009/0270960 A1 | 10/2009 | Zhao et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0125313 A1 | 5/2010 | Lee et al. |
| 2010/0137938 A1 | 6/2010 | Kishawi et al. |
| 2010/0152811 A1 | 6/2010 | Flaherty |
| 2010/0185253 A1 | 7/2010 | Dimarco et al. |
| 2010/0217355 A1 | 8/2010 | Tass et al. |
| 2010/0241191 A1 | 9/2010 | Testerman |
| 2010/0274312 A1 | 10/2010 | Alataris |
| 2010/0312304 A1 | 12/2010 | York et al. |
| 2011/0034977 A1 | 2/2011 | Janik et al. |
| 2011/0054567 A1 | 3/2011 | Lane |
| 2011/0054568 A1 | 3/2011 | Lane |
| 2011/0077660 A1 | 3/2011 | Janik et al. |
| 2011/0130804 A1 | 6/2011 | Lin et al. |
| 2011/0160810 A1 | 6/2011 | Griffith |
| 2011/0184489 A1 | 7/2011 | Nicolelis et al. |
| 2011/0218590 A1 | 9/2011 | Degiorgio et al. |
| 2011/0218594 A1 | 9/2011 | Doron |
| 2011/0224665 A1 | 9/2011 | Crosby et al. |
| 2011/0224753 A1 | 9/2011 | Palermo |
| 2011/0224757 A1 | 9/2011 | Zdeblick et al. |
| 2011/0237921 A1 | 9/2011 | Askin et al. |
| 2012/0035684 A1 | 2/2012 | Thompson et al. |
| 2012/0059432 A1 | 3/2012 | Emborg et al. |
| 2012/0071950 A1 | 3/2012 | Archer |
| 2012/0109251 A1 | 5/2012 | Lebedev |
| 2012/0123293 A1 | 5/2012 | Shah et al. |
| 2012/0136408 A1 | 5/2012 | Grill et al. |
| 2012/0165899 A1 | 6/2012 | Gliner |
| 2012/0172946 A1 | 7/2012 | Altaris et al. |
| 2012/0179222 A1 | 7/2012 | Jaax |
| 2012/0203131 A1* | 8/2012 | DiLorenzo ......... A61B 5/04001 600/544 |
| 2012/0232615 A1 | 9/2012 | Barolat |
| 2012/0277834 A1 | 11/2012 | Mercanzini et al. |
| 2012/0330391 A1 | 12/2012 | Bradley et al. |
| 2013/0030501 A1 | 1/2013 | Feler et al. |
| 2013/0035745 A1 | 2/2013 | Ahmed et al. |
| 2013/0085361 A1 | 4/2013 | Mercanzini et al. |
| 2013/0096640 A1 | 4/2013 | Possover |
| 2013/0123568 A1 | 5/2013 | Hamilton et al. |
| 2013/0253299 A1 | 9/2013 | Weber |
| 2013/0253611 A1 | 9/2013 | Lee |
| 2014/0163640 A1 | 6/2014 | Edgerton et al. |
| 2014/0180361 A1 | 6/2014 | Burdick |
| 2014/0316484 A1 | 10/2014 | Edgerton |
| 2014/0316503 A1 | 10/2014 | Tai |
| 2015/0217120 A1 | 8/2015 | Nandra et al. |
| 2015/0231396 A1 | 8/2015 | Burdick et al. |
| 2016/0030748 A1 | 2/2016 | Edgerton et al. |
| 2016/0121109 A1 | 5/2016 | Edgerton et al. |
| 2016/0175586 A1 | 6/2016 | Edgerton et al. |
| 2016/0220813 A1 | 8/2016 | Edgergton et al. |
| 2016/0310739 A1 | 10/2016 | Burdick et al. |
| 2017/0157389 A1 | 6/2017 | Tai et al. |
| 2018/0229037 A1 | 8/2018 | Edgerton et al. |
| 2018/0229038 A1 | 8/2018 | Burdick et al. |
| 2018/0353755 A1 | 12/2018 | Edgerton et al. |

FOREIGN PATENT DOCUMENTS

| | | |
|---|---|---|
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | 1997/047357 A1 | 12/1997 |
| WO | 2003/026735 A2 | 4/2003 |
| WO | 2003/092795 A1 | 11/2003 |
| WO | 2004/087116 A2 | 10/2004 |
| WO | 2005/051306 A2 | 6/2005 |
| WO | 2005/087307 A2 | 9/2005 |
| WO | 2007/081764 A2 | 7/2007 |
| WO | 2007/107831 A2 | 9/2007 |
| WO | 2008/070807 A3 | 6/2008 |
| WO | 2008/075294 A1 | 6/2008 |
| WO | 2008/109862 A2 | 9/2008 |
| WO | 2008/121891 A1 | 10/2008 |
| WO | 2009/042217 A1 | 4/2009 |
| WO | 2009/111142 A2 | 9/2009 |
| WO | 2010/114998 A1 | 10/2010 |
| WO | 2010/124128 A1 | 10/2010 |
| WO | 2011/005607 A1 | 1/2011 |
| WO | 2012/094346 A2 | 7/2012 |
| WO | 2012/100260 A2 | 7/2012 |
| WO | 2012/129574 A2 | 9/2012 |
| WO | 2013/071307 A1 | 5/2013 |
| WO | 2013/071309 A1 | 5/2013 |
| WO | 2014/144785 A1 | 9/2014 |
| WO | 2015/106286 A1 | 7/2015 |

OTHER PUBLICATIONS

Office Action for Australian Patent Application No. 2017221868 dated Jan. 23, 2018.

Office Action for Canadian Patent Application No. 2,825,550 dated Jan. 24, 2018.

U.S. Office Action for U.S. Appl. No. 14/925,791 dated Jul. 20, 2017.

U.S. Office Action for U.S. Appl. No. 15/096,014 dated Sep. 14, 2017.

Ganley et al., Epidural spinal cord stimulation improves locomoter performance in low ASIA C, Wheel-chair-Dependent, spinal cord-injured individuals: Insights from metabolic response. Top. Spinal Cord Inj. Rehabil; 11(2); 50-63 (2005).

"Hermann et al., Spinal cord stimulation facilitates functional walking in a chronic, incomplete spinal cord injured. Spinal Cord, vol. 40, pp. 65-68 (2002)."

International Search Report for International Application Serial No. PCT/US2012/020112 filed on Jan. 3, 2012.

(56) References Cited

OTHER PUBLICATIONS

International Search Report for International Application Serial No. PCT/US2012/022257 filed on Jan. 23, 2012.
International Search Report for International Application Serial No. PCT/US2012/030624 filed on Mar. 26, 2012.
International Search Report for International Application Serial No. PCT/US2014/029340 filed on Mar. 14, 2014.
Nandra et al., A parylene-based microelectrode array implant for spinal cord stimulation in rats. Conf. Proc. IEEE Eng. Med. Biol. Soc., pp. 1007-1010 (2011).
Nandra et al., A wireless microelectode implant for spinal cord stimulation and recording in rats. Presentation Abstract, 2013.
Transcutaneous Lumbar Spinal Cord Stimulation, http://www.restrorativeneurology.org (available online and attached), International Society for Restorative Neurology, 2012.
Rodger et al., High density flexible parylene-based multielectrode arrays for retinal and spinal cord stimulation. Proc. Of the 14th International Conference on Solid-State Sensors, Actuators and Microsystems, pp. 1385-1888 (2007).
International Search Report for International Application Serial No. PCT/US2012/064874 filed on Nov. 13, 2012.
International Search Report for International Application Serial No. PCT/US2012/064878 filed on Nov. 13, 2012.
Dimitrijevic et al., Clinical elements for the neuromuscular stimulation and functional electrical stimulation protocols in the practice of neurorehabilitation, Artificial Organs, 26(3): 256-259 (2002).
Dimitrijevic et al., Evidence for a spinal central pattern generator in humans. Annals New York Academy Sciences, 860: 360-376 (1998).
Gerasimenko et al., Control of locomotor activity in humans and animals in the absence of supraspinal influences. Neuroscience and Behavioral Physiology, 32(4): 417-423 (2002).
Hofstoetter et al., Modification of reflex responses to lumbar posterior root stimulation by motor tasks in healthy subjects. Artificial Organs, 32(8):644-648 (2008).
Hofstoetter et al., Model of spinal cord reflex circuits in humans: stimulation frequency-dependence of segmental activities and their interactions. Second Congress International Society of Intraoperative Neurophysiology (ISIN), Dubrovnik, Croatia, pp. 8-10 (2009).
International Search Report and Written Opinion dated May 19, 2015 for International Application Serial No. PCT/US2015/011263 filed on Jan. 13, 2015.
Jilge et al, Initiating extension of the lower limbs in subjects with complete spinal cord injury by epidural lumbar cord stimulation. Exp Brain Res., 154: 308-326 (2004).
Ladenbauer et al., Stimulation of the human lumbar spinal cord with implanted and surface electrodes: a computer simulation study. IEEE Transactions on Neural Systems and Rehabilitation Engineering, 18(6):637-645 (2010).
Minassian et al., Transcutaneous stimulation of the human lumbar spinal cord: Facilitating locomotor output in spinal cord injury. Society for Neuroscience, Conference Proceedings, Neuroscience 2010, San Diego, CA, Abstract Viewer/Itinerary Planner No. 286.19, Abstract & Poster attached (2010).
Minassian et al., Human lumbar cord circuitries can be activated by extrinsic tonic input to generate locomotor-like activity. Human Movement Science, 26(2):275-295 (2007).
Minassian et al., Posterior root-muscle reflexes elicited by transcutaneous stimulation of the human lumbosacral cord. Muscle & Nerve, 35(3):327-336 (2007) Article first published online in 2006.
Minassian et al., Stepping-like movements in humans with complete spinal cord injury induced by epidural stimulation of the lumbar cord: electromyographic study of compound muscle action potentials. Spinal Cord, 42:401-416 (2004).
Minassian et al., Peripheral and central afferent input to the lumbar cord. Biocybernetics and Biomedical Engineering, 25(3): 11-29 (2005).
Minassian et al., Human lumbar cord model of the locomotor central pattern generator. Second Congress International Society of Intraoperative Neurophysiology (ISIN), Dubrovnik, Croatia, pp. 11-13 (2009).
Minassian et al., Posterior root-muscle reflex, Second Congress International Society of Intraoperative Neurophysiology (ISIN), Dubrovnik, Croatia, pp. 77-80 (2009).
Murg et al., Epidural electric stimulation of posterior structures of the human lumbar spinal cord: 1. Muscle twitches—a functional method to define the site of stimulation. Spinal Cord, 38: 394-402 (2000).
Rattay et al., Epidural electrical stimulation of posterior structures of the human lumbosacral cord: 2. Quantitative analysis by computer modeling. Spinal Cord, 38: 473-489 (2000).
Supplementary European Search Report and Opinion for European Patent Application Serial No. 12848368.2 filed on Nov. 13, 2012.
Ward, Electrical Stimulation Using Kilohertz-Frequency Alternating Current. Physical therapy, 89:181-190 (2009) (published online Dec. 18, 2008).
Minassian et al., Neurophysiology of the human lumbar locomotor pattern generator. 2010. 15th Annual Conference of the International Functional Electrical Stimulation Society. Annual IFESS Conference Proceedings.
Gerasimenko et al., Noninvasive reactivation of motor descending control after paralysis. Journal of Neurotrauma, 2015 (article has been peer-reviewed and accpeted for publication, 49 pages).
Danner et al., Body position influences which neural structures are recruited by lumbar transcutaneous spinal cord stimulation. PLoS ONE 11(1):e0147479 (2016).
Dimitrijevic et al., Electrophysiological characteristics of H-reflexes elicited by percutaneous stimulation of the cauda equina. Abstract No. 4927, 34th Annual Meeting of the Society for Neuroscience, San Diego, CA (2004).
Hofstoetter et al., Modification of spasticity by transcutaneous spinal cord stimulation in individuals with incomplete spinal cord injury. The Journal of Spinal Cord Medicine, 37:2, 202-211 (2014).
Hofstoetter et al., Effects of transcutaneous spinal cord stimulation on voluntary locomotor activity in an incomplete spinal cord injured individual. Biomed Tech, 58 (Suppl. 1) 2013.
Krenn et al., Selectivity of transcutaneous stimulation of lumbar posterior roots at different spinal levels in humans. Biomed Tech, 58 (Suppl. 1) (2013).
Minassian et al., Mechanisms of rhythm generation of the human lumbar spinal cord in repose to tonic stimulation without and with step-related sensory feedback. Biomed Tech, 58 (Suppl. 1) (2013).
Minassian et al., Neuromodulation of lower limb motor control in restorative neurology. Clinical Neurology and Neurosurgery, 114:489-497 (2012).
Office Action for European Patent Application No. 12760696.0 dated Nov. 9, 2017.
Office Action for Canadian Patent Application No. 2,823,592 dated Oct. 5, 2017.
Office Action for Australian Patent Application No. 2017203132 dated Oct. 13, 2017.
Rasmussen, Carl Edward. Gaussian Processes in Machine Learning. Machine Learning, L.N.A.I. 3176, p. 63-71 (2003).
U.S. Appl. No. 15/878,325, filed Jan. 23, 2018.
U.S. Appl. No. 15/821,076, filed Nov. 22, 2017.
Examination Report for Australian Patent Application No. 2017202237 dated Apr. 6, 2018.
U.S. Appl. No. 15/940,473, filed Mar. 29, 2018.
Office Action for Canadian Patent Application No. 2,856,202 dated Jun. 19, 2018.
Office Action for European Patent Application No. 12848368.2 dated May 9, 2018.
Office Action for Canadian Patent Application No. 2,823,592 daed Aug. 20, 2018.
Office Action for Canadian Patent Application No. 2,824,782 dated Oct. 2, 2018.
Office Action for Canadian Patent Application No. 2,825,550 dated Dec. 20, 2018.
Office Action for European Patent Application No. 12732280.8 dated Aug. 24, 2018.
Office Action for Korean Patent Application No. 10-2013-7027989 dated Dec. 14, 2018 (original and translation included).
U.S. Office Action for U.S. Appl. No. 15/232,623 dated Dec. 26, 2018.

(56) References Cited

OTHER PUBLICATIONS

Office Action for Japanese Patent Application No. 2017-198155 dated Sep. 11, 2018 (original and translation enclosed).
Office Action for Chinese Patent Application No. 201610987062.5 dated Sep. 30, 2018 (original and translation enclosed).
U.S. Office Action for U.S. Appl. No. 15/821,076 dated Oct. 10, 2018.
U.S. Appl. No. 16/189,655, filed Nov. 13, 2018.
U.S. Appl. No. 16/153,472, filed Oct. 5, 2018.
Office Action for Canadian Patent Application No. 2,823,592 dated Aug. 20, 2018.

* cited by examiner

NEUROMODULATION SYSTEMS AND METHODS OF USING SAME

CROSS REFERENCE TO RELATED APPLICATIONS

This application is a continuation of U.S. patent application Ser. No. 14/596,118, filed Jan. 13, 2015, which claims the benefit of U.S. provisional patent application No. 61/926,457, filed Jan. 13, 2014, the entire disclosures each of which is incorporated herein by reference.

GOVERNMENT LICENSE RIGHTS

This invention was made with government support under Grant No. EB007615 awarded by the National Institutes of Health. The government has certain rights in the invention.

SUMMARY

Described herein generally are neuromodulation systems. The systems can include a programmable controller wirelessly communicatively coupled to a host computer, a signal generator communicatively coupled to the controller, and a plurality of electrodes and/or sensors communicatively coupled to the signal generator. In some embodiments, the controller, in cooperation with the signal generator and the at least one electrode can be configured to deliver a stimulation to a mammal based on an instruction received from the host computer, the stimulation thereby inducing voluntary movement and/or enabling restoration of function.

In other embodiments, the neuromodulation systems can include a multiplexer circuit configured to enable the processor to select a first pair of the electrodes to deliver the stimulation. The multiplexer circuit can be configured to enable the processor to select a second pair of electrodes to sense an electrical signal within the mammal.

In some embodiments, the stimulator system can receive a signal or signals from one or more electrodes or pairs of electrodes (or other communicatively coupled sensors/devices/systems)

In some embodiments, the neuromodulation systems can further comprise a wireless power receiver. The wireless power receiver can be configured to: receive power wirelessly from a wireless power supply; and rectify the received power into at least one DC voltage for the controller and the signal generator.

The neurostimulation systems can induce voluntary movements of a foot, a toe, an ankle, a knee, a leg, a hip, a shoulder, an arm, a wrist, a hand, a finger, a waist, a trunk, a neck, a head, or a combination thereof. The voluntary movement can include at least one of standing, stepping, a walking motor pattern, sitting down, sitting up, laying down, reaching, grasping, pulling and pushing, swallowing and chewing, breathing, and coughing. In some embodiments the neurostimulation system can induce or enable the restoration of function of a targeted organ, organ system, or a cell or cell body making up an organ or organ system.

The neurostimulation systems can be used to apply stimulation over a cervical portion of the spinal cord or the brainstem. The delivered signal can be applied epidurally over at least one of a thoracic, a thoraco-lumbar, a lumbar portion, a lumbosacral portion, and a sacral portion of the spinal cord.

Methods of inducing movement, e.g., voluntary movement using the herein described neurostimulation systems are also described. Methods of inducing a voluntary movement in a mammal with a spinal injury can comprise: receiving in a programmable controller from a wirelessly communicatively coupled host computer an instruction to apply a stimulation to a mammal; instructing a signal generator via the controller to apply the stimulation; and applying via the signal generator to at least one electrode the stimulation including a monophasic or biphasic signal and/ or a mono-polar or bi-polar stimulus.

The methods can further include transmitting a control instruction from the programmable controller to a multiplexer circuit to select the at least one electrode for applying the stimulation.

In some embodiments, selecting the electrode can include selecting a pair or pairs of electrodes within a MEMS microelectrode array, electromyography ("EMG") wires, or EMG electrodes.

The methods can further include transmitting a control instruction from the controller to a multiplexer circuit to select the at least one electrode to sense an electrical signal within the mammal. The at least one electrode selected may be from within the same microelectrode array, another microelectrode array and/or a sensor. The sensor may include a pressure sensor, a temperature sensor, a chemical sensor, a flow sensor, a flex sensor, a gyroscope, or an accelerometer.

In some embodiments, the methods can further include receiving power wirelessly in a wireless power receiver from a wireless power supply; and rectifying the received power in a DC voltage for the controller and the signal generator.

In still other embodiments, the methods can further include determining in the controller that received power is insufficient for the stimulation; and transmitting a message to the wireless power receiver for additional power.

Neuromodulation systems are also described including: a controller configured to wirelessly receive operating instructions from a host computer; a signal generator communicatively coupled to the controller; a multiplexer circuit communicatively coupled to the controller and the signal generator; a wireless power receiver electrically coupled to a wireless power supply and configured to power the controller, the signal generator, the multiplexer circuit; a plurality of EMG wires electrically coupled to the multiplexer circuit; and a microelectrode array including (but not limited to) a 9×3 array of electrodes electrically coupled to the multiplexer circuit. In some embodiments, the controller, in cooperation with the signal generator, the multiplexer circuit, and at least one of an EMG wire and an electrode within the microelectrode array are configured to deliver a stimulation (e.g., an epidural stimulation) to a mammal, the stimulation being configured to induce voluntary movement or enable restoration of a function in the mammal.

In some embodiments, the multiplexer circuit can be configured to enable a pair of the EMG wires or a pair or pairs of the electrodes within the microelectrode array to receive the stimulation from the signal generator.

Additional features and advantages are described herein, and will be apparent from the following Detailed Description and figures.

DETAILED DESCRIPTION

Figure 1:
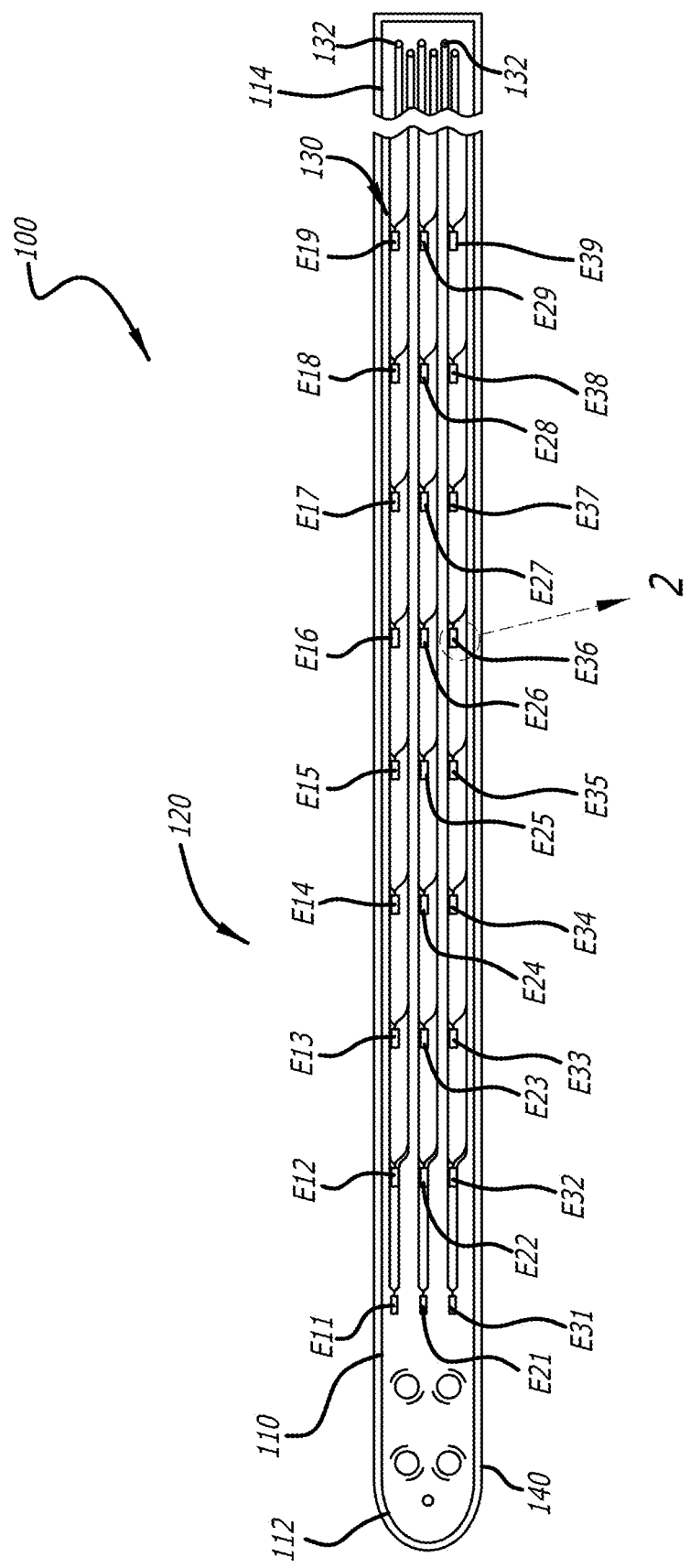
FIG. 1 shows a diagram of a view of an underside of an implantable electrode array assembly, according to an example embodiment of the present disclosure.

The present disclosure relates in general to the field of neurological treatment and rehabilitation for injury and disease including traumatic spinal cord injury, non-traumatic spinal cord injury, stroke, movement disorders, brain injury, and other diseases or injuries that result in paralysis and/or nervous system disorder. Neuromodulation systems, devices, and methods are provided to facilitate recovery of posture, locomotion, and voluntary movements such as those of the fingers, hands, arms, trunk, legs, and feet and recovery of autonomic, sexual, vasomotor, speech, swallowing, chewing, respiratory and cognitive function, in a human subject having spinal cord injury, brain injury, or any other neurological disorder or impairment. In some embodiments, the systems can include wireless communications.

The neuromodulation systems can include: a controller wirelessly communicatively coupled to a host computer; a signal generator communicatively coupled to the controller; and a plurality of electrodes communicatively coupled to the signal generator. In some embodiments, the controller, in cooperation with the signal generator and the at least one electrode can be configured to deliver a stimulation to a mammal based on an instruction received from the host computer, the stimulation including being configured to induce voluntary movement or enable restoration of function.

The use of conventional wire electrodes for spinal cord stimulation can be effective in facilitating locomotor recovery in rats that have lower body paralysis. The use of a MEMS high-density microelectrode array may offer greater selectivity and flexibility in stimulation patterns, allowing for optimization of hindlimb stepping motion and better study of electrophysiological changes following the spinal cord injury. However, in some circumstances, 37 wires are needed for this passive implant and can often cause health complications.

Although active electronics have been implemented to reduce the number of wires, the present devices, e.g., implants, and systems present a fully wireless spinal cord implant. In some embodiments, this wireless implant can be for mammals. In other embodiments, the implant can be for humans.

This wireless spinal cord implant can include an epidural microelectrode array and optional electrodes for evoked potentials and/or sensors.

The herein described implant is capable or can be configured to both stimulate and record spinal cord, EMG responses, evoked potentials, sensory evoked potentials, or a type of physiological signal (i.e. electrical, chemical, photonic, mechanical, acoustic, etc.) from a subjects body or body parts (i.e. organ or organ system or the cells that make up the organ or organ system). Additionally, the implant (by way of non-limiting example) may be part of a closed loop system. In other embodiments the implant may communicate with other systems and devices either implanted or external to the body such as, for example, a pharmaceutical pump or a robotic system.

In one example embodiment, the wireless implant can include a 9×3 MEMS microelectrode array, a PCB with wireless microprocessor/transceiver, EMG wires, a power coil configured to receive power wirelessly, and sealing materials.

The microelectrode, by way of a non-limiting example, can be fabricated with a parylene-metal-parylene sandwich structure. The microelectrode can incorporate an improved microelectrode design and other additions to improve mechanical reliability and minimize delamination while retaining flexibility. The PCB can fit 22 IC chips and about 100 passive components into a compact having a 10 mm×32 mm footprint.

In some embodiments, the microelectrode array can include a plurality of electrodes. Each individual electrode within the plurality of electrodes can be pulsed or stimulated individually. In some embodiments, electrodes can be pulsed in pairs. A pair can include two or more individual electrodes group together. In some embodiments, an electrode or groups of electrodes can also be configured to record electrical signals.

The stimulator associated with the wireless implant can be configured to send a stimulating pulse to any pair of electrodes in the electrode array. In some embodiments, the stimulator system can receive a signal or signals from one or more electrodes or pairs of electrodes (or other communicatively coupled sensors/devices/systems). In other embodiments, the electrode array can include more than 2 electrodes, more than 5 electrodes, more than 10 electrodes, more than 15 electrodes, more than 20 electrodes, more than 25 electrodes, more than 30 electrodes, more than 50 electrodes, more than 100 electrodes, more than 500 electrodes, more than 1,000 electrodes, more than 5,000 electrodes, more than 10,000 electrodes, between about 2 electrodes and about 10,000 electrodes, between about 25 electrodes and about 35 electrodes, or between about 25 electrodes and about 100 electrodes. In some embodiments, the electrode array can include 27 electrodes, 54 electrodes, 108 electrodes, 216 electrodes, or more.

In some embodiments, the circuitry encased in the wireless electrode can switch between different electrode pairs very rapidly, this circuitry can be configured to effectively send an arbitrary pattern of pulses to a multi-electrode array or other electrode array as described herein.

In one embodiment, the systems described can address 27 electrodes, two reference wires, and 16 EMG wires.

In some embodiments, the systems can include a maximum stimulating voltage. This maximum stimulating voltage can be achieved in a constant voltage mode. Example stimulating voltages can be about ±5 V, about ±6 V, about ±7 V, about ±8 V, about ±9 V, about ±10 V, about ±11 V, about ±12 V, about ±13 V, about ±14 V, about ±15 V, about ±20 V, at least about ±5 V, at least about ±10 V, at least about ±12 V, between about ±5 V and about ±20 V, or between about ±10 V and about ±15 V. In one embodiment, the maximum stimulating voltage can be ±12V.

In some embodiments, the systems can include a maximum stimulating current. This maximum stimulating current can be achieved in a constant current mode. Maximum stimulating currents can be about ±1 mA, about ±2 mA, about ±3 mA, about ±4 mA, about ±5 mA, about ±6 mA, about ±7 mA, about ±8 mA, about ±9 mA, about ±10 mA, at least about ±1 mA, at least about ±2 mA, at least about ±4 mA, between about ±1 mA and about ±10 mA, or between about ±4 mA and about ±6 mA. In one embodiment, the maximum stimulating current can be ±5 mA.

In embodiments, the systems can provide an arbitrary waveform stimulation. Arbitrary waveform stimulation can be about 10 kHz, about 20 kHz, about 30 kHz, about 40 kHz, about 50 kHz, about 60 kHz, about 70 kHz, about 80 kHz, about 90 kHz, about 100 kHz, about 110 kHz, about 120 kHz, about 130 kHz, about 140 kHz, about 150 kHz, about 160 kHz, about 170 kHz, about 180 kHz, about 190 kHz, about 200 kHz, at least about 50 kHz, at least about 80 kHz, at least about 90 kHz, between about 10 kHz and about 200 kHz, or between about 90 kHz and about 110 kHz. In one embodiment, the arbitrary waveform stimulation can be 100 kHz.

The systems can provide virtually any pulsed waveform. The pulsed waveform can be as low as about 0.1 ms pulse width, as high as 50 kHz frequency with a recording bandwidth up to about 60 kHz (−3 dB).

The herein described systems can provide a digital-to-analog (DAC) resolution between about 5 bits and about 15 bits, between about 6 bits and about 13 bits, or between about 7 bits and about 12 bits.

The systems can have a characteristic configuration switch time. Characteristic switch times can be about 1 μs, about 2 μs, about 3 μs, about 4 μs, about 5 μs, about 6 μs, about 7 μs, about 8 μs, about 9 μs, about 10 μs, less than about 10 μs, less than about 8 μs, less than about 4 μs, between about 1 μs and about 10 μs, or between about 2 μs and about 4 μs. In one embodiment, the maximum stimulating current can be 3 μs.

The systems can configure and pulse a number of times per given time period. In some embodiments, the systems can configure and pulse about 10 times/millisecond (ms), about 20 times/ms, about 30 times/ms, about 40 times/ms, about 50 times/ms, about 60 times/ms, about 70 times/ms, about 80 times/ms, about 90 times/ms, about 100 times/ms, about 110 times/ms, about 120 times/ms, about 130 times/ms, about 140 times/ms, about 150 times/ms, about 160 times/ms, about 170 times/ms, about 180 times/ms, about 190 times/ms, about 200 times/ms, at least about 10 times/ms, at least about 20 times/ms, at least about 40 times/ms, at least about 60 times/ms, at least about 80 times/ms, at least about 100 times/ms, between about 10 times/ms and about 200 times/ms, or between about 90 times/ms and about 110 times/ms. In one embodiment, the systems can configure and pulse 100 times/ms.

The systems can be configured to simultaneously address a given number of electrodes. In some embodiments, the electrodes can be arbitrary. In one embodiment, the systems can simultaneously address 2 electrodes, 4 electrodes, 6 electrodes, 8 electrodes, 10 electrodes, 12 electrodes, 14 electrodes, 16 electrodes, 18 electrodes, 20 electrodes, or any group of electrodes. Further, the system can simultaneously address 2 arbitrary electrodes, 4 arbitrary electrodes, 6 arbitrary electrodes, 8 arbitrary electrodes, 10 arbitrary electrodes, 12 arbitrary electrodes, 14 arbitrary electrodes, 16 arbitrary electrodes, 18 arbitrary electrodes, 20 arbitrary electrodes, or more arbitrary electrodes. In some embodiments, the systems can simultaneously address up to 8 arbitrary electrodes with limited configuration flexibility.

Further, the systems can be configured such that any two electrodes, if not used for stimulating, can be chosen as the differential pair for recording. Thus, any two electrodes not being used for stimulation can be used for recording. However, the recording electrodes are not limited to two at a time. The systems can be configured to allow 4 electrodes, 6 electrodes, 8 electrodes, 10 electrodes, 12 electrodes, 14 electrodes, 16 electrodes, 18 electrodes, 20 electrodes, or more electrodes to be used for recording.

The systems can communicate wirelessly and possess characteristic data transfer rates. For example, the systems can have wireless data transfer rates of about 250 kBps, 500 kBps, 750 kBps, 1,000 kBps, at least 250 kBps, at least 500 kBps, between about 250 kBps and about 500 kBps, between about 250 kBps and about 1,000 kBps, or between about 250 kBps and about 750 kBps. These data rates can be on ISM band 915 MHz. In one example embodiment, the systems can have wireless data transfer rates of about 250 kBps.

The systems can also be configured as low power drawing systems. The max power consumption of the systems can be less than about 100 mW, less than about 90 mW, less than about 80 mW, less than about 70 mW, less than about 60 mW, less than about 50 mW, less than about 40 mW, less than about 30 mW, or less than about 20 mW. In one embodiment, the systems use less than about 100 mW of power when active.

FIG. 1 illustrates an implantable electrode array assembly 100, according to an example embodiment of the present disclosure. While the embodiment of the assembly 100 illustrated is configured for implantation in a rat, embodiments may be constructed for use in other subjects, such as other mammals, including humans, and such embodiments are within the scope of the present teachings. The assembly 100 is for use with a subject that has a spinal cord 330 (see FIG. 3) with at least one selected spinal circuit (not shown) and a neurologically derived paralysis in a portion of the subject's body. By way of a non-limiting example, the assembly 100 may be implanted epidurally along the spinal cord 330. The assembly 100 may be positioned at one or more of a sacral region, lumbosacral region, a lumbar region, a thoraco-lumbar region, a thoracic region, and/or a cervical region of the spinal cord 330 or a brainstem.

By way of non-limiting examples, when activated, the selected spinal circuit may (a) enable voluntary movement of muscles involved in at least one of standing, stepping, reaching, grasping, chewing, swallowing, breathing, voluntarily changing positions of one or both legs, voiding the subject's bladder, voiding the subject's bowel, postural activity, sitting, and locomotor activity; (b) enable or improve autonomic control of at least one of cardiovascular function, body temperature, and metabolic processes; and/or (c) help facilitate recovery of at least one of an autonomic function, sexual function, vasomotor function, and cognitive function. Without being limited by theory, it is believed that the selected spinal circuit has a first stimulation threshold representing a minimum amount of stimulation required to activate the selected spinal circuit, and a second stimulation threshold representing an amount of stimulation above which the selected spinal circuit is fully activated and adding the induced neurological signals has no additional effect on the at least one selected spinal circuit.

The paralysis may be a motor complete paralysis or a motor incomplete paralysis. The paralysis may have been caused by a spinal cord injury classified as motor complete or motor incomplete. The paralysis may have been caused by an ischemic or traumatic brain injury. The paralysis may have been caused by an ischemic brain injury that resulted from a stroke or acute trauma. By way of another example, the paralysis may have been caused by a neurodegenerative brain injury. The neurodegenerative brain injury may be associated with at least one of Parkinson's disease, Huntington's disease, Alzheimer's, ischemia, stroke, amyotrophic lateral sclerosis (ALS), primary lateral sclerosis (PLS), and cerebral palsy.

If the paralysis was caused by a spinal cord injury at a first location along the spinal cord 330, the assembly 100 may be implanted (e.g., epidurally) at a second location below the first location along the spinal cord relative to the subject's brain (not shown).

The example assembly 100 is configured to apply electrical stimulation to a portion of a spinal cord 330 of a subject. The electrical stimulation may include at least one of tonic stimulation and intermittent stimulation. The stimulation applied may be pulsed. The electrical stimulation may include simultaneous or sequential stimulation of different regions of the spinal cord. The electrical stimulation applied by the assembly 100 may be below the second stimulation threshold such that the at least one selected spinal circuit is at least partially activatable by the addition of signals generated by the subject. By way of a non-limiting example, such subject generated signals may be induced by subjecting the subject to physical activity or training (such as stepping on a treadmill). These signals may be induced in a paralyzed portion of the subject. By way of another non-limiting example, the subject generated signals may include supraspinal signals.

Figure 2:
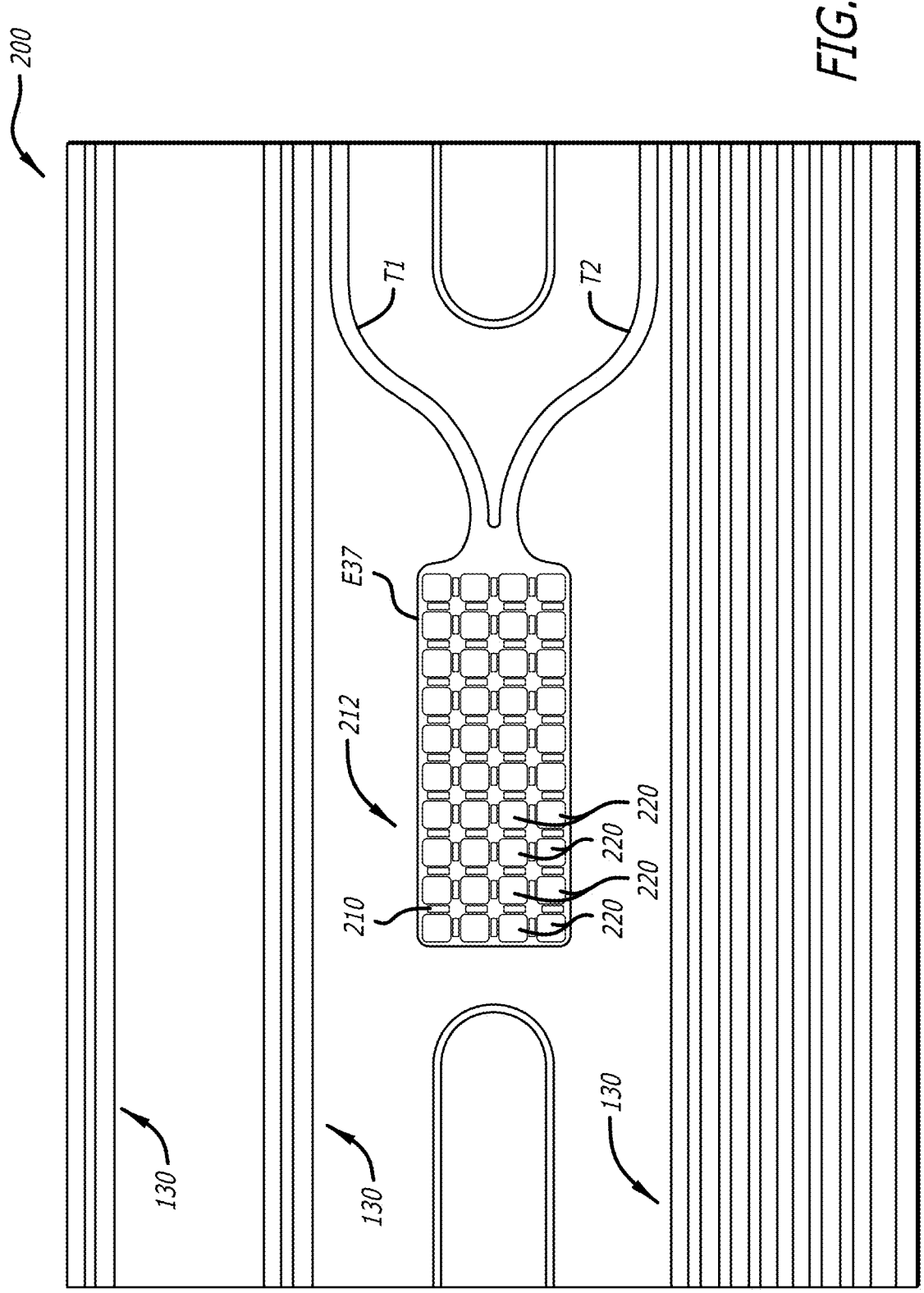
FIG. 2 shows a diagram of an enlarged view of a portion of the assembly of FIG. 1, according to an example embodiment of the present disclosure.
Figure 3:
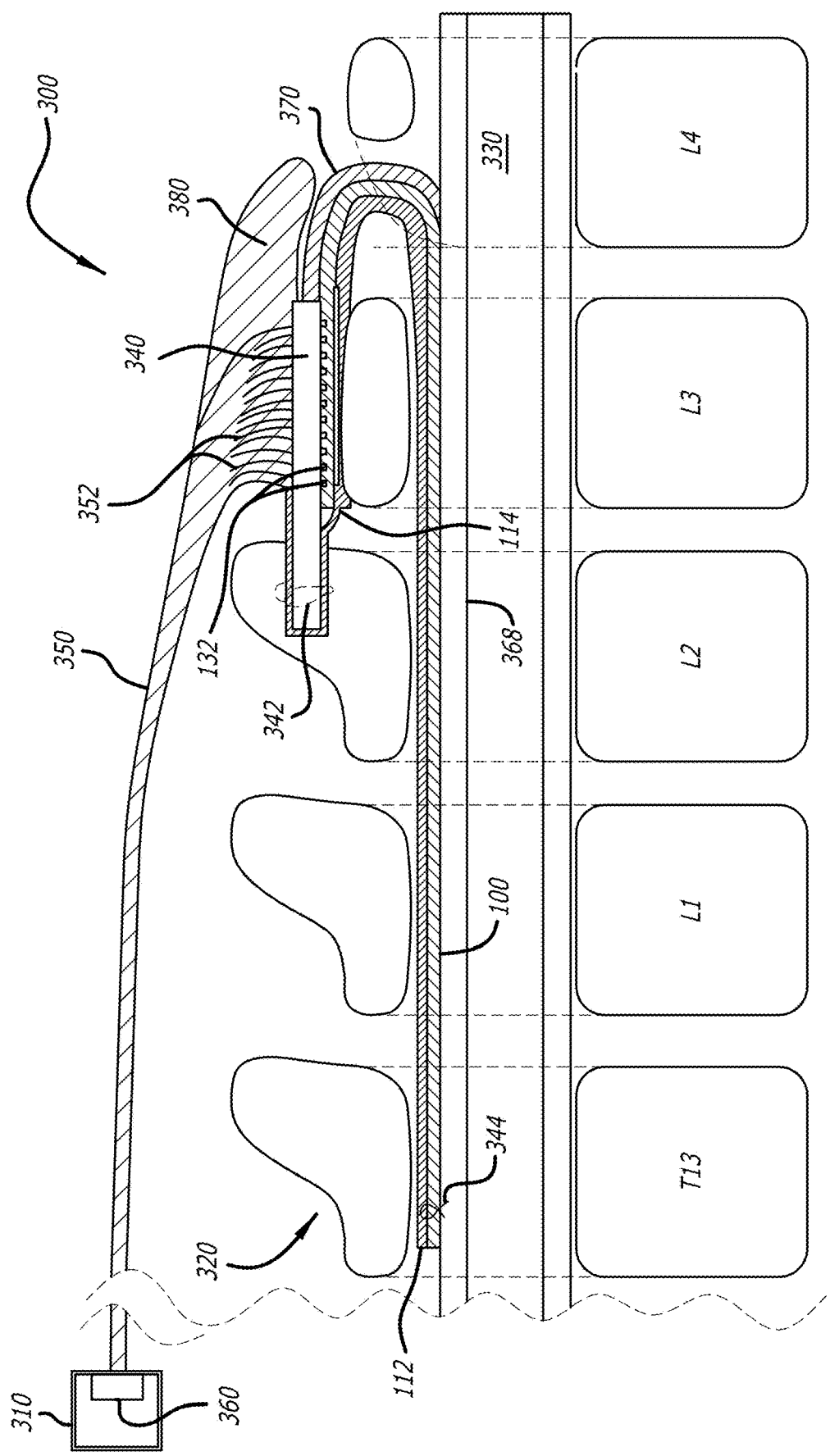
FIG. 3 shows a diagram of a cross-sectional view of a cable system incorporating the assembly of FIG. 1, according to an example embodiment of the present disclosure.

In one embodiment, the assembly 100 illustrated in FIGS. 1 to 3 can be configured for implantation in a rat. Thus, in some embodiments of the assembly 100 illustrated, the implant can be sized (e.g., about 59 mm by about 3 mm) and shaped for implantation into the rat. However, embodiments may be constructed for use with other subjects, such as other mammals, including humans.

FIG. 2 illustrates an enlarged portion 200 of the assembly 100 depicted in FIG. 1, according to an example embodiment of the present disclosure. The assembly 100 may be characterized as being a microelectromechanical systems ("MEMS") device. As mentioned above, the assembly 100 is configured for implantation along the spinal cord 330 (see FIG. 3) and to provide electrical stimulation thereto. For example, the assembly 100 may provide epidural stimulation to the spinal cord 330. The assembly 100 enables a high degree of freedom and specificity in selecting the site of stimulation compared to prior art wire-based implants, and triggers varied biological responses that can lead to an increased understanding of the spinal cord 330 and locomotive, movement, autonomic and functional recovery for victims of spinal cord injury.

Turning to FIG. 1, the assembly 100 includes a body portion 110, an electrode array 120, and a plurality of electrically conductive traces 130. The body portion 110 includes a distal end portion 112, a proximal end portion 114 (opposite the distal end portion), a frame 140, and a grid structure 210 (see FIG. 2) for each electrode E11-E19, E21-E29, and E31-E39 of the electrode array 120. Each of the grid structures 210 defines a plurality of cells 212. By way of a non-limiting example, the grid structures 210 may each be constructed from parylene (e.g., parylene-C). In the embodiment illustrated, the grid structure 210 includes 40 cells.

As mentioned above, the electrode array 120 includes the plurality of electrodes E11-E19, E21-E29, and E31-E39 (e.g., 9×3 electrodes). The electrodes E11-E19, E21-E29, and E31-E39 are arranged in a two-dimensional array. Each of the electrodes E11-E19, E21-E29, and E31-E39 includes a plurality of electrically conductive contacts 220. The contacts 220 are sites at which the electrode (e.g., the electrode E37 illustrated in FIG. 2) will contact the spinal cord (e.g., the dura). The contacts 220 are in electrically communication with one another. The embodiment of the electrode E37 illustrated includes 40 contacts 220. However, this is not a requirement. As mentioned above, each of the electrodes E11-E19, E21-E29, and E31-E39 corresponds to a unique one of the grid structures 210. In the embodiment illustrated, for each of the electrodes E11-E19, E21-E29, and E31-E39, each of the contacts 220 is positioned within a different one of the cells 212 of the corresponding grid structure 210. The grid structure 210 may help prevent delamination of the layers of the assembly 100 (see FIG. 1). The grid structure 210 and contacts 220 may be formed by selectively etching a layer of substantially electrically non-conductive material (e.g., parylene) adjacent a pad of electrically conductive material (e.g., metal such as platinum or gold) to define the grid structure 210 and expose portions of the electrically conductive material within the cells 212 of the grid structure to define the contacts 220.

While the electrode array 120 illustrated includes 27 electrodes, in other embodiments, the number of electrodes may range from one electrode to about 1000 electrodes or more. As discussed above, the electrode array 120 includes at least 10, at least 15, at least 20, at least 25, at least 50, at least 100, at least 250, at least 500, or at least 1000 electrodes. In various embodiments, the inter-electrode spacing of adjacent electrodes in the electrode array 120 varies from about 100 μm or about 500 μm, or about 1000 μm or about 1500 μm to about 2000 μm, or about 3000 μm, or about 4000 μm, or about 4500 μm, or about 5000 μm. In various embodiments, inter-electrode spacing ranges from about 100 μm, about 150 μm, about 200 μm, or about 250 μm up to about 1,000 μm, about 2000 μm, about 3000 μm, or about 4,000 μm. In some embodiments, the diameter (or width) of each of the electrodes E11-E19, E21-E29, and E31-E39 ranges from about 50 μm, 100 μm, 150 μm, 200 μm, or 250 μm up to about 500 μm, about 1000 μm, about 1500 μm, or about 2000 μm.

The electrode array 120 can be formed in any geometric shape such as a square shape, rectangular shape, circular shape, tubular shape, fan shape, or fusiform shape. Typically the size of the electrode array 120 will be on the order of about 0.1 mm to about 2 cm, wide or in diameter, depending in part on the number of electrodes in the electrode array 120. In various embodiments, the length of the electrode array 120 ranges from about 0.01 mm, or 0.1 mm up to about 10 cm or greater.

One or more of the traces 130 is connected to each of the electrodes E11-E19, E21-E29, and E31-E39. Referring to FIG. 2, in the embodiment illustrated, two traces "T1" and "T2" are connected to each of the electrodes E11-E19, E21-E29, and E31-E39. In alternate embodiments, more than two traces 130 may be connected to each of the electrodes E11-E19, E21-E29, and E31-E39. Connecting more than one of the traces 130 to each of the electrodes E11-E19, E21-E29, and E31-E39 helps ensure signals reach each of the electrodes E11-E19, E21-E29, and E31-E39. In other words, redundancy may be used to improve reliability. For each of the electrodes E11-E19, E21-E29, and E31-E39, the traces 130 are connected to each of the contacts 220 of the electrode and carry or receive signals thereto. Openings 132 (see FIG. 3) formed (e.g., etched) in the body portion 110 expose portions of the traces 130.

The traces 130 may be used to selectively deliver electrical signals (e.g., pulsed signals) to (or record signals from) the electrodes E11-E19, E21-E29, and E31-E39. In this manner, only a selected one or more of the electrodes (or pair of electrodes) E11-E19, E21-E29, and E31-E39 may deliver stimulation to the spinal cord 330 (see FIG. 3). The electrodes E11-E19, E21-E29, and E31-E39 are operably linked by the traces 130 to control circuitry, as discussed in further detail below. The control circuitry is configured to select one or more of the electrodes E11-E19, E21-E29, and E31-E39 to activate/stimulate/record and/or to control the parameters (e.g., frequency, pulse width, amplitude, etc.) of the electrical stimulation. In various embodiments, the electrode selection, frequency, amplitude, and pulse width are independently selectable. For example, at different times, different electrodes can be selected. At any time, different electrodes can provide stimulation having different parameter values (e.g., frequencies, amplitudes, and the like). In various embodiments, at least a portion of the electrodes may be operated in a monopolar mode and/or a bipolar mode. In such embodiments, constant current or constant voltage may be used to deliver the stimulation.

In some embodiments, the traces 130 may receive signals from implantable control circuitry and/or an implantable power source (not shown). The implantable control circuitry may be programmed and/or reprogrammed by an external device (e.g., using a handheld device that communicates with the control circuitry through the skin). The programming may be repeated as often as necessary.

FIG. 3 illustrates a cable system 300 incorporating the assembly 100 of FIG. 1, according to an example embodiment of the present disclosure. The example cable system 300 is illustrated implanted along the spine 320 and spinal cord 330 of a rat. The cable system 300 is composed of a spinal baseplate 340, EMG wires 350, and/or EMG electrodes 310. The baseplate 340 may be constructed from a FR-4 PCB substrate. The baseplate 340 is attached (e.g., by a suture 342) to a selected vertebrae (e.g., vertebrae "L2"). In the embodiment illustrated, the baseplate 340 is attached to the "L2" vertebrae. The assembly 100 is attached (e.g., by a suture 344) to the spinal cord 300. In the embodiment illustrated, the distal end portion 112 of the assembly 100 is attached to the spinal cord 300 at a location adjacent vertebrae "T13." The proximal end portion 114 of the assembly 100 is attached to the baseplate 340 using a conductive material (e.g., conductive epoxy) to bridge electrical connections. By way of a non-limiting example, the proximal end portion 114 of the assembly 100 may be secured to the baseplate 340 using Loctite M-121HP Medical device epoxy.

The example EMG wires 350 may be connected to hind limbs or other structure of a subject for inducing electrical stimulation or recording one or more signals. The EMG wires 350 may be connected to or include one or more EMG electrodes 310. In some embodiments, the EMG wires 350 may be replaced with connections to other types of electrodes, sensors, and/or systems/devices either wired or wireless, or may also be omitted.

The EMG wires 350 include a plurality of wires 352. By way of a non-limiting example, the wires 352 may each be connected to a separate electrode 310. Each of the wires 352 may be constructed from gold and include a Teflon coating. For example, 75 µm gold wires (e.g., Teflon coated gold wire manufactured by AM Systems) may be used. The wires 352 may be soldered to the baseplate 340 and connected by high density connectors 360 to the respective electrodes 310. The traces 130 are connected to the baseplate 340 via the openings 132 formed in the body portion 110 of the assembly 100. By way of a non-limiting example, silver epoxy (not shown) may be used to connect the traces 130 to the baseplate 340.

Figure 4:
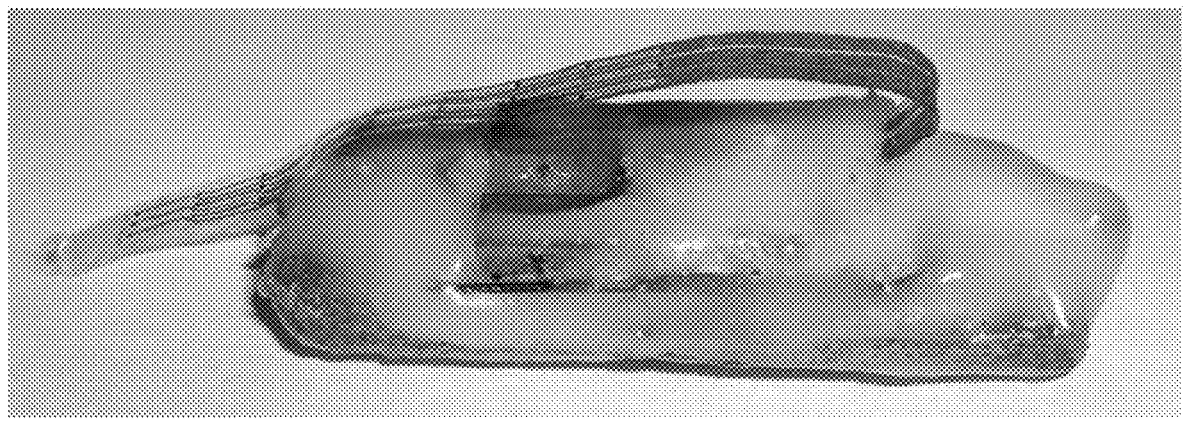
FIG. 4 shows a diagram of the cable system of FIG. 3 coated with a coating, according to an example embodiment of the present disclosure.

As shown in FIG. 4, the entire cable system 300 (except a portion 368 of the assembly 100) may be coated with a coating 370 configured to insulate electrical connections and provide mechanical strength while retaining the flexibility wherever necessary. The implants described herein can be covered and/or sealed to prevent exposure of the implant or portions of the implant to tissues. In some embodiments, the entire implant can be covered or sealed. In other embodiments, substantially all of the implant is coated or sealed.

In one embodiment, the implant can be sealed using a combination of parylene, an epoxy and a silicone. In some embodiments, the implant can be sealed by coating it in silicone. In other embodiments, an epoxy can be used to seal the implant, in still other embodiments, parylene can be used to seal the implant. Parylene is used to describe a variety of chemical vapor deposited poly(p-xylylene) polymers used as moisture and dielectric barriers. In one example embodiment, parylene-C is used to seal the implant. Combinations of epoxy, parylene and silicone can be used to seal the implant.

By way of a non-limiting example, the coating 370 may include a biomedical grade epoxy and a silicone elastomer (e.g., MDX 4-4210 Biomedical grade silicone).

Further, commercially available, hermetic metal packaging cannot satisfy size and feed-through requirements for the presently described wireless implants. New metal packaging and feed-through assemblies can be mechanically designed, manufactured and incorporated. However, in some embodiments, a new sealing technique can be used to encase the wireless implants. The technique used to seal the wireless implants can use parylene-C, epoxy, and/or silicone.

In some embodiments, components of the implant can be attached using an epoxy and then completely coated with silicone. In other embodiments, components of the implant can be attached using an epoxy and then completely coated with parylene. The implant can be coated by methods such as dipping, brushing, spray coating, rolling, vapor deposition, and the like. In one example embodiment, the implant can be sealed by dipping the implant in a coating solution. The coating solution can include epoxy, silicone, and/or parylene. In some embodiments, the implant can be covered in an epoxy, for example, by dipping and then coated with parylene, silicone or a combination thereof.

The sealed wireless implant can remain sealed in vivo for a useful lifetime of the implant. In some embodiments, the wireless implant can remain sealed for at least one month, at least two months, at least three months, at least four months, at least five months, at least six months, at least one year, at least two years, at least five years, between about two months and about 5 years, between about 1 year and about 5 years, or between about 6 months and about 5 years. In one embodiment, the technique of sealing the wireless implant can provide sufficient sealing for at least two months of in vivo functionality.

A silicone cap 380 (or overhanging portion) is formed on the end of the baseplate 340 to protect the assembly 100 from external moving tissue. The cap 380 may be formed from the same material as the coating 370. Along portions of the assembly 100, the coating 370 may be implemented as a thin layer of silicone (e.g., about 100 µm thick) to reduce stress concentration as the assembly 100 bends with the subject's spine 320 during movement. A thicker layer of silicone applied to the assembly 100 may be detrimental to the health of the spinal cord 330 because of increased pressure that is applied by a more rigid assembly to the spinal cord. In other words, flexibility may be an important feature of a successful chronic implantable electrode array assembly.

Figure 5:
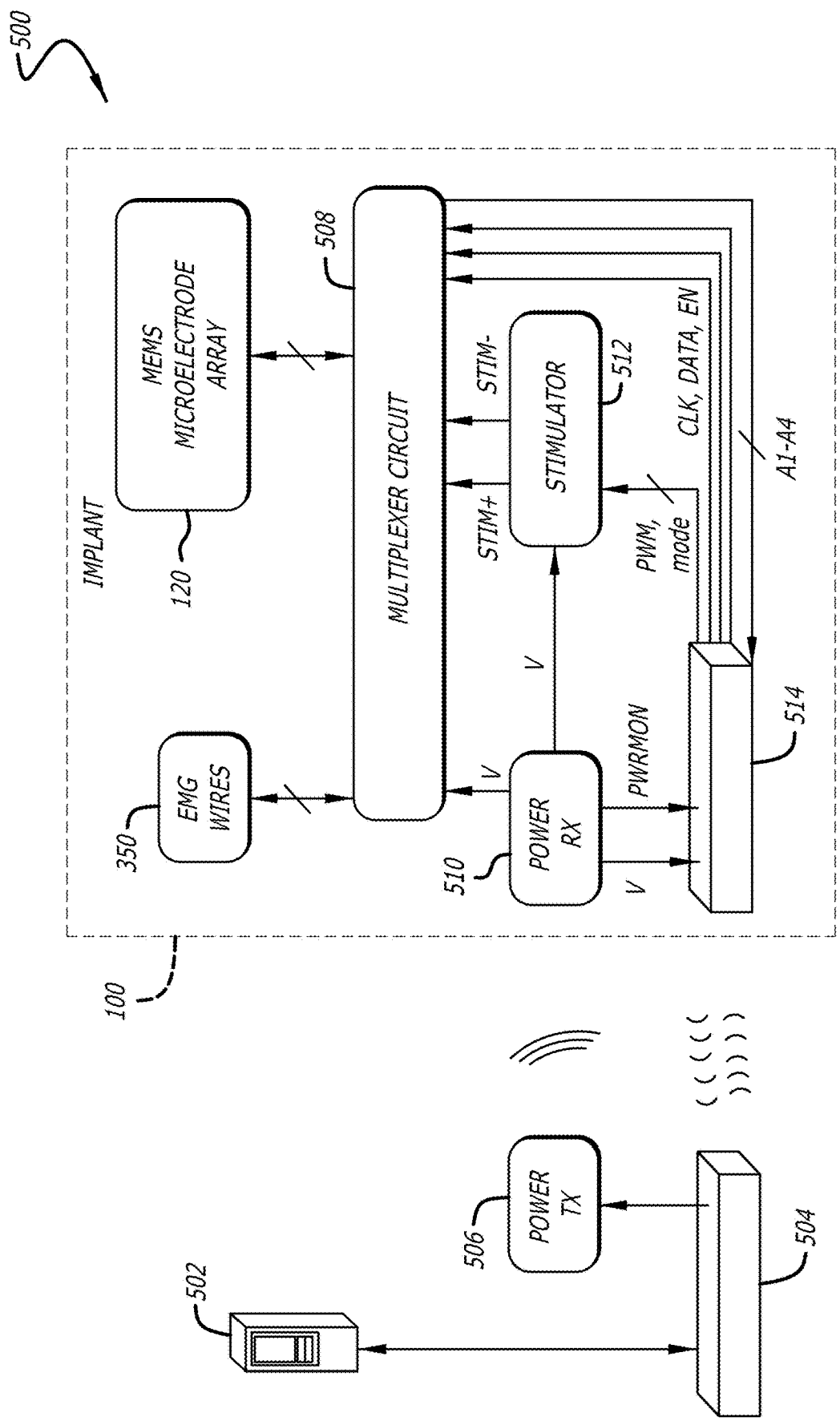
FIG. 5 shows a diagram of an example implant system including the implantable electrode array assembly and cable system of FIGS. 1 to 3, according to an example embodiment of the present disclosure.

FIG. 5 shows a diagram of an example implant system 500, according to an example embodiment of the present disclosure. The example implant system 500 includes the example implantable electrode array assembly 100 discussed above in conjunction with FIGS. 1 to 4. The system 500 also includes a host computer 502 that is configured to be communicatively coupled to the implantable electrode array assembly 100. The example host computer 502 may include any computer, laptop computer, server, workstation, processor, tablet computer, smartphone, smart-eyewear, smart-watch, lab instrument, etc. The host computer 502 may be centralized or distributed via a network or cloud computing environment. In some embodiments, the host computer 502 may include an interface, which enables remote devices (e.g., smartphones) to remotely specify data (or instructions) to be transmitted to the implantable electrode array assembly 100 and view data received from the implantable electrode array assembly 100.

The example host computer 502 is configured to determine and/or control data streams for transmission to the implantable electrode array assembly 100. In some instances, a user may specify the data streams (or instructions) to be transmitted. In other instances, the host computer 502 may include machine-readable instructions, which when executed, cause the host computer 502 to operate one or more algorithms for determining data streams to be transmitted to the implantable electrode array assembly 100. The host computer 502 is also configured to receive, process, and/or analyze data streams from the implantable electrode array assembly 100. In some instances, the host computer 502 may include machine-readable instructions, which when executed, cause the host computer 502 to operate one or more algorithms that analyze received data streams from the implantable electrode array assembly 100. The host computer 502 may also be configured to provide a graphical representation indicative of the data streams transmitted to the implantable electrode array assembly 100 and/or a graphical representation indicative of the data streams received from the implantable electrode array assembly 100.

To facilitate communication between the host computer 502 and the assembly 100, the example implant system 500 includes a controller 504. In other embodiments, to facilitate communication between the host computer 502 and the assembly 100, the example implant system 500 may include a controller 504 The example controller 504 includes a transceiver configured to convert communications from the host computer 502 into a wireless format (e.g., a low power RF format, Bluetooth®, Zigbee®, etc.) for transmission to the assembly 100. The example controller 504 is also configured to receive wireless signals (e.g., wireless streams of data) from the assembly 100 and convert the wireless signals into a format compatible for the host computer 502. In some instances, the controller 504 is communicatively coupled to the host computer 502 via a Universal Serial Bus ("USB"). In other embodiments, the controller 504 is communicatively coupled wirelessly to the host computer 502. The controller 504 may also include memory to buffer or queue data streams for transmission. In an embodiment, the controller 504 (by way of a non-limiting example) may include the Texas Instruments® CC1111 Sub-1 GHz RF System-on-Chip.

The example system 500 also includes a wireless power supply 506 configured to provide wireless power to the assembly 100. The power supply 506 is communicatively coupled to at least one of the host computer 502 and/or the controller 504 to receive power control instructions. The example wireless power supply 506 may include a Class E amplifier and inductive coupling components to enable wireless transmission of power to the assembly 100 (as discussed further in conjunction with FIG. 7). The example wireless power supply 506 may also include a variable output to enable the amount of power provided to the assembly 100 to be adjusted based on, for example, application of the assembly 100, power requirements of the assembly 100, and/or operations being performed by the assembly 100. For example, the host computer 502 may instruct the wireless power supply 506 to output relatively more wireless power when relatively more stimulation signals are to be provided by the assembly 100.

As discussed above, the example implantable electrode array assembly 100 includes EMG wires 350, a MEMS microelectrode array 120, and implantable control circuitry. In the example embodiment of FIG. 5, the implantable control circuitry includes a multiplexer circuit 508, a wireless power receiver 510, a stimulator 512 (e.g., a signal generator/receiver), and a controller 514. It should be appreciated that the implantable control circuitry of the assembly 100 may include additional or fewer components. For example, the implantable control circuitry may also include a battery for long term storage of power from the wireless power supply 506, a memory to store instructions for operation of the implantable control circuitry, a memory to store data streams transmitted from the host computer 502 and/or detected by the assembly 100, etc. Further, the implantable control circuitry of FIG. 5 may be combined and/or partitioned differently based on hardware used, application, etc.

The example wireless power receiver 510 (discussed further in conjunction with FIG. 7) is configured to receive wireless power from the wireless power supply 506 and convert the wireless power into a DC voltage. In some embodiments, the wireless power receiver 510 is configured to output 3 V DC and 12 V DC. In other embodiments, the wireless power receiver 510 may output 5 V DC. It should be appreciated that the wireless power receiver 510 may be configured to output one or more different DC voltages having any magnitude based, for example, on power requirements of the other implantable control circuitry, electromagnetic considerations of the assembly, etc. The wireless power receiver 510 may also output an AC signal and/or a power monitor signal (e.g., PWRMON) based on requirements of the implantable control circuitry. For instance, the wireless power receiver 510 is configured to output a power monitor signal to the controller 514 to enable the controller 514 to monitor power received from the wireless power supply 506.

The example controller 514 (discussed further in conjunction with FIG. 8) is configured to operate instructions that control the multiplexer circuit 508 and/or the stimulator 512. The controller 514 includes a transceiver configured to receive a data stream wirelessly from the controller 504 and convert the wireless data stream for processing. The example controller 514 may also include instructions that instruct the controller 514 how to control the multiplexer circuit 508 and/or the stimulator 512 based on the data stream generated by the host computer 502. For example, after receiving a data stream that indicates that electrode pair E13 and E33 are to be stimulated with a waveform having a specified amplitude, shape, frequency, etc., the controller 514 transmits the appropriate signal (e.g., appropriate digital word) via Clock, Data, and EN (enable) lines to the multiplexer circuit 508 to cause the specified waveform (e.g., stimulation signal) to be provided by the E13 and E33 electrode pair of the MEMS microelectrode array 120.

In other instances, the example controller 514 is configured to be programmed with operating instructions from the host computer 502 via the controller 504. The operating instructions may specify the stimulation signal(s) and timing that is to be controlled and/or managed by the controller 514. Such a configuration enables the controller 514 to provide stimulation signals as specified without having the controller 504 and/or host computer 502 in constant contact or proximity of the subject.

The example controller 514 can also be configured to record amplified signals (e.g., signals A1-A4) received from the EMG wires 350, EMG electrodes 310, the MEMS microelectrode array 120, or other electrodes, sensors, or systems. In some embodiments, a sensor or system may wirelessly provide an indication of a recoded signal. For instance, the host computer 502 may specify within a data stream that electrodes E18 and E39 are to sense or otherwise detect an electrical signal after stimulation by another electrode pair. The controller 514 is configured to transmit the appropriate signal (e.g., appropriate digital word) via Clock, Data, and EN (enable) lines to the multiplexer circuit 508 to cause voltages detected by the E18 and E39 electrodes of the MEMS microelectrode array 120 to be amplified and recorded. In other embodiments, the host computer 502 may specify within a data stream that electrodes and/or sensors 350 are to record signal(s). The controller 514 is configured to transmit the appropriate signal (e.g., appropriate digital word) via Clock, Data, and EN (enable) lines to the multiplexer circuit 508 to cause voltages detected by the electrodes and/or sensors to be amplified and recorded. The controller 514 may then transmit the recorded data via a data stream to the transceiver 504.

The example controller 514 can also be configured to monitor the wireless power received at the wireless power receiver 510. For instance, the controller 514 is configured to enable that enough power is provided to enable the multiplexer circuit 508 to output the specified stimulating pulses to the subject. In one example, the controller 514 may receive within a data stream a sequence of pulses to be applied to the subject and determine that the power being received at the wireless power receiver 510 is insufficient. In response, the controller 514 may transmit a message to the transceiver 504 for additional power (or an amount of additional power needed), which causes the controller 504 to increase the amount of power output by the wireless power supply 506. In an embodiment, the controller 514 may include the Texas Instruments® CC1111 Sub-1 GHz RF System-on-Chip.

The example stimulator 512 (discussed further in conjunction with FIG. 9) is configured to provide a constant voltage and/or current to the multiplexer circuit 508. The constant voltage and/or current is provided via a Stim+ and a Stim− signal lines to the multiplexer circuit 508. The amount of voltage and/or current provided by the stimulator 512 may be set via a pulse width modulation ("PWM") signal from the controller 514. The amount of voltage provided may be based on a stimulation signal specified by the host computer 502. A mode between voltage and current output may be set via a mode signal from the controller 514.

Figure 6:
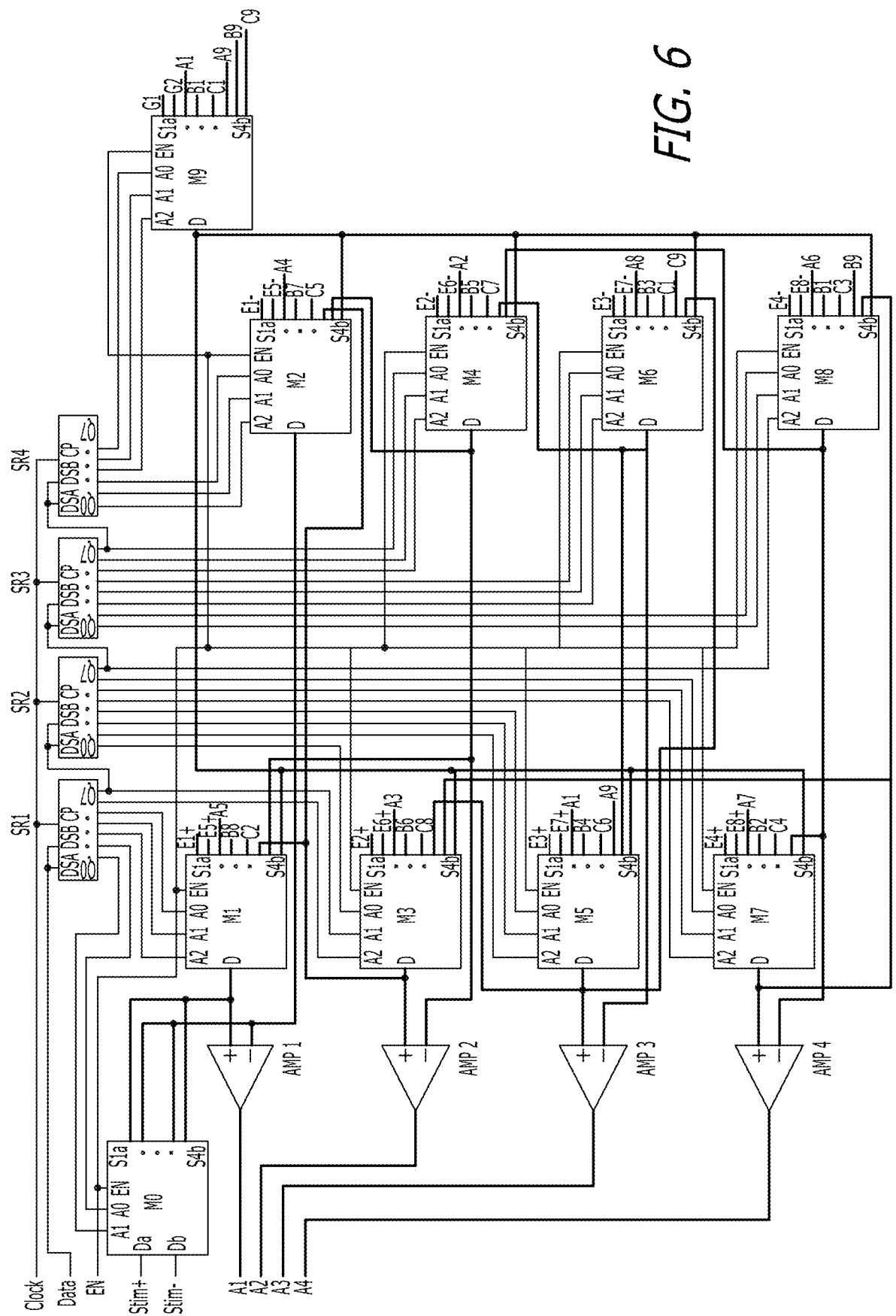
FIG. 6 shows a diagram of a multiplexer circuit, according to an example embodiment of the present disclosure.

The example multiplexer circuit 508 is configured to route connections between the stimulator 512 and/or amplifiers and the EMG wires 350, the EMG electrodes 310, the MEMS microelectrode array 120, or other types of electrodes, sensors, systems, devices, etc. FIG. 6 shows a diagram of the multiplexer circuit 508, according to an example embodiment of the present disclosure. The example multiplexer circuit 508 includes multiplexers M0, M1, M2, M3, M4, M5, M6, M7, M8, and M9, which may include Analog Devices® ADG1209 or ADG1208 multiplexers. The multiplexer circuit 508 also includes shift registers SR1, SR2, SR3, and SR4, which may include NXP Semiconductors® 74HC164 shift registers. The multiplexer circuit 508 further includes amplifiers AMP1, AMP2, AMP3, and AMP4, which may include Analog Devices AD8224 amplifiers. The multiplexer circuit 508 receives as control inputs from the controller 514 Clock, Data, and EN, which specify which of the EMG wires 350, the EMG electrodes 310, the electrode pair within MEMS microelectrode array 120, or other types of electrodes, sensors, systems, devices, etc. are to be configured to output a stimulation signal (e.g., Stim+ or Stim−) and/or configured to receive an electrical signal. The multiplexer circuit 508 receives the stimulation signals Stim+ and Stim− from the stimulator 512.

The desired configuration can be achieved by sending, for example, a 30-bit serial data stream through the Clock and Data inputs into the shift registers SR1 to SR4. The example shift registers SR1 to SR4 in turn control or select which output of the multiplexers M1 to M9 are to receive and output the Stim+ and Stim− signals. The EN signal is used by the controller 514 to enable the multiplexers M0 to M9. The example multiplexer M0 is configured to disconnect the stimulation wires to the multiplexers M1 to M9 in instances where the controller 514 instructs the multiplexer circuit 508 to configure the EMG wires 350 and/or the MEMS microelectrode array 120 to record. The multiplexer M0 is also configured to select a polarity of the stimulation signal to be provided to any one of the multiplexers M1 to M9 in instances where the controller 514 instructs that a stimulation signal is to be output to a subject.

The example multiplexers M1 to M9 are configured to receive control signals from the shift registers SR1 to SR4 to determine which output is to receive a stimulation signal. As shown in FIG. 6, the multiplexers M1 to M9 are interconnected to enable almost any two of the electrodes within the MEMS microelectrode array 120, the EMG wires 350, the EMG electrodes 310, or other types of electrodes, sensors, systems, devices, etc. to be selected for outputting a stimulation signal or detecting an electrical signal within the subject. The illustrated embodiment shows the multiplexers M1 to M9 connected to an electrodes designated by an alpha-numeric identifier. The letter "E" refers to an EMG wire 350 where "E #+" and "E #" are EMG wire pairs. The letters "A", "B", and "C" refer to spinal cord electrode columns shown in FIG. 1, where the letter "A" corresponds to column 1, the letter "B' corresponds to column 2, and the letter "C" corresponds to the column 3. Thus, A3 refers to the electrode E13 of the MEMS microelectrode array 120 of FIG. 1. Outputs G1 and G2 refer to reference wires placed, for example, near the shoulder and the lower back respectively on a subject. The multiplexer M1 is configured to be selectively connected to E1+, E5+, A5, B8, and C2. The multiplexer M2 is configured to be selectively connected to E1−, E55, A4, B7, and C5. The multiplexer M3 is configured to be selectively connected to E2+, E6+, A3, B6, and C8. The multiplexer M4 is configured to be selectively connected to E2−, E6−, A2, B5, and C7. The multiplexer M5 is configured to be selectively connected to E3+, E7+, A1, B4, C6, and A9. The multiplexer M6 is configured to be selectively connected to E3−, E7−, A8, B3, C1, and C9. The multiplexer M7 is configured to be selectively connected to E4+, E8+, A7, B2, and C4. The multiplexer M8 is configured to be selectively connected to E4−, E8−, A6, B1, C3, and B9. Finally, the multiplexer M9 is configured to be selectively connected to G1, G2, A1, B1, C1, A9, B9, and C9. It should be appreciated that some key electrodes (e.g., the electrodes corresponding to A9, B9, and C9) have two connections or outputs within the multiplexer circuit 508 to further increase electrode pairing configurations. It should be appreciated that the number of multiplexers and/or multiplexer outputs may change based on the number of EMG wires 350 and/or electrodes within the MEMS microelectrode array 120.

The example amplifiers AMP 1 to AMP 4 are configured to amplify a differential signal received from selected ones of the EMG wires 350, the EMG electrodes 310, electrodes within the MEMS microelectrode array 120, and/or other types of electrodes, sensors, systems, devices, etc. Each of the amplifiers AMP1 to AMP4 may be configured to have a gain of 200 and output respective signals A1 to A4 representative of detected electrical pulses within a subject. For example, the controller 514 may instruct the multiplexer circuit 508 to enter a 'listen mode' where the E1+ and E1− EMG wires 350 and/or EMG electrodes 310 (or other types of electrodes, sensors, systems, devices, etc.) are set to record or otherwise sense an electrical signal and convey this signal via multiplexers M1 and M2 to one or more of the amplifiers AMP1 to AMP4, for transmission to the controller 514.

The example multiplexer circuit 508 of FIG. 6 may be configured to operate in four different modes to meet experimental requirements. A first mode enables a simulation signal to be applied by any two electrodes within the MEMS microelectrode array 120, the EMG wires 350, and/or the EMG electrodes 310. A second mode enables the multiplexer circuit 508 to record from any four EMG wire pairs, EMG electrodes, or other types of electrodes, sensors, systems, devices, etc. A third mode enables the multiplexer circuit 508 to record from any two electrodes within the array 120. A fourth mode enables the multiplexer circuit 508 to record from four electrodes of the same column within the array 120 with respect to a fifth electrode. The example multiplexer circuit 508 is configured to switch between the different modes and configurations of selected electrodes of the array 120 and/or EMG wires 350 or EMG electrodes 310 within 1 microsecond, thereby enabling the Stim+ and Stim− stimulation signals to delivery relatively short pulses to many electrodes and/or EMG wires or EMG electrodes in a one millisecond timeframe. Such a configuration also enables the amplifiers AMP1 to AMP4 to rapidly switch input signals to effectively record from eight or sixteen signals instead of four within a specified timeframe.

Figure 7:
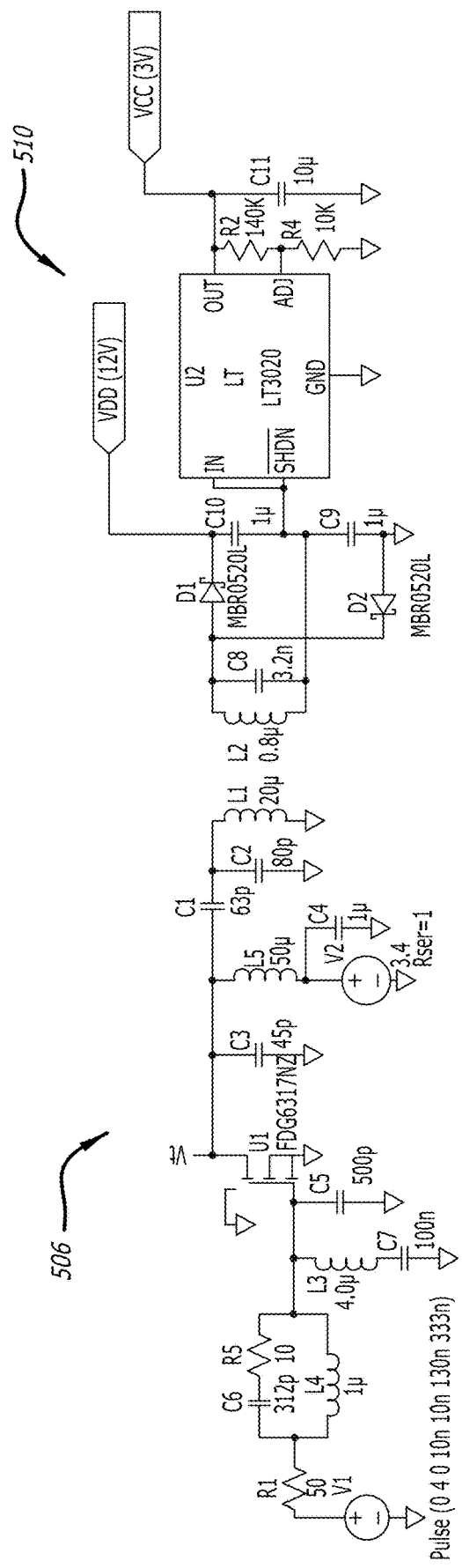
FIG. 7 shows a diagram of a wireless power supply and a wireless power receiver, according to an example embodiment of the present disclosure.

FIG. 7 shows a diagram of the example wireless power supply 506 and the wireless power receiver 510 of FIG. 5, according to an example embodiment of the present disclosure. As illustrated, the example wireless power supply 506 uses inductor L1 to convert power provided by supply V1 for transmission via a wireless medium. The wireless power supply 506 also includes circuitry to convert the voltage from supply V1 into an AC signal. The example wireless power supply 510 uses indictor L2 to receive the power and convert the power into an AC signal. The wireless power supply 510 also includes a voltage regulator U2 and circuitry D1, D2, C9, and C10 configured to convert or rectify the AC signal into one or more DC voltages (e.g., 3 V and 12 V).

Figure 8:
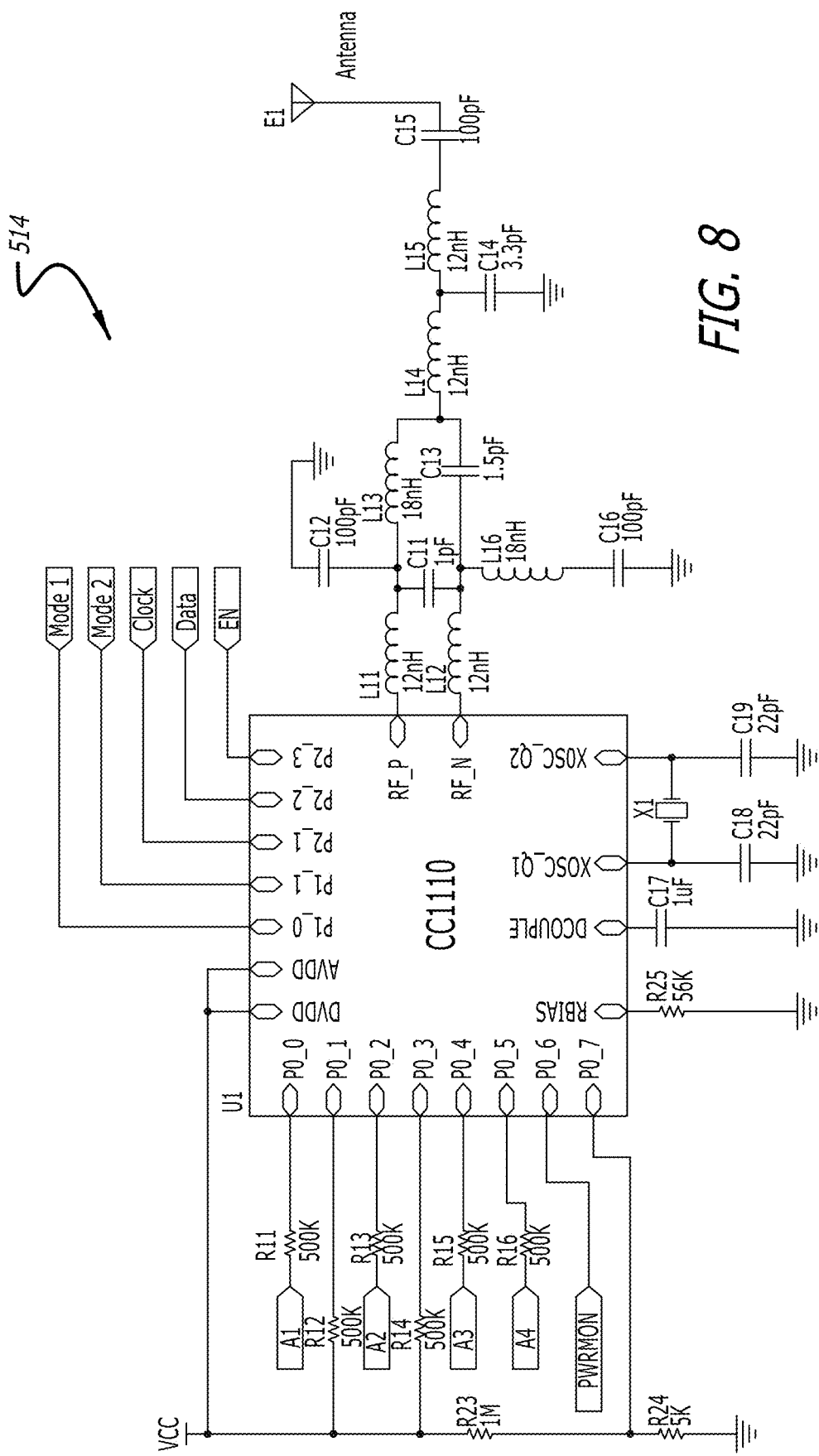
FIG. 8 shows a diagram of a controller, according to an example embodiment of the present disclosure.

FIG. 8 shows a diagram of the example controller 514 of FIG. 5, according to an example embodiment of the present disclosure. The example controller 514 is wirelessly communicatively coupled to the controller 504 via antenna E1 and corresponding circuitry. As described above in conjunction with FIGS. 5 and 6, the example controller 514 is configured to instruct the stimulator 512 to operate in a voltage or current mode via the Mode1 and Mode2 outputs and instruct the multiplexer circuit 508 via the Clock, Data, and EN outputs. The example controller 514 receives one or more detected signals via inputs A1 to A4.

The example controller 514 may include memory to enable instructions to be stored from the host computer 502 specifying how and types of stimulation pulses are to be applied to a subject. The example controller 514 may include memory to enable instructions to be stored from the host computer 502 specifying which electrodes and/or EMG wires/electrodes (or other types of electrodes, sensors, systems, devices, etc.) are to be used for recording electrical signals. The example controller 514 may include memory to store a data structure of operations including when pulses were applied and data representative of data received via inputs A1 to A4.

Figure 9:
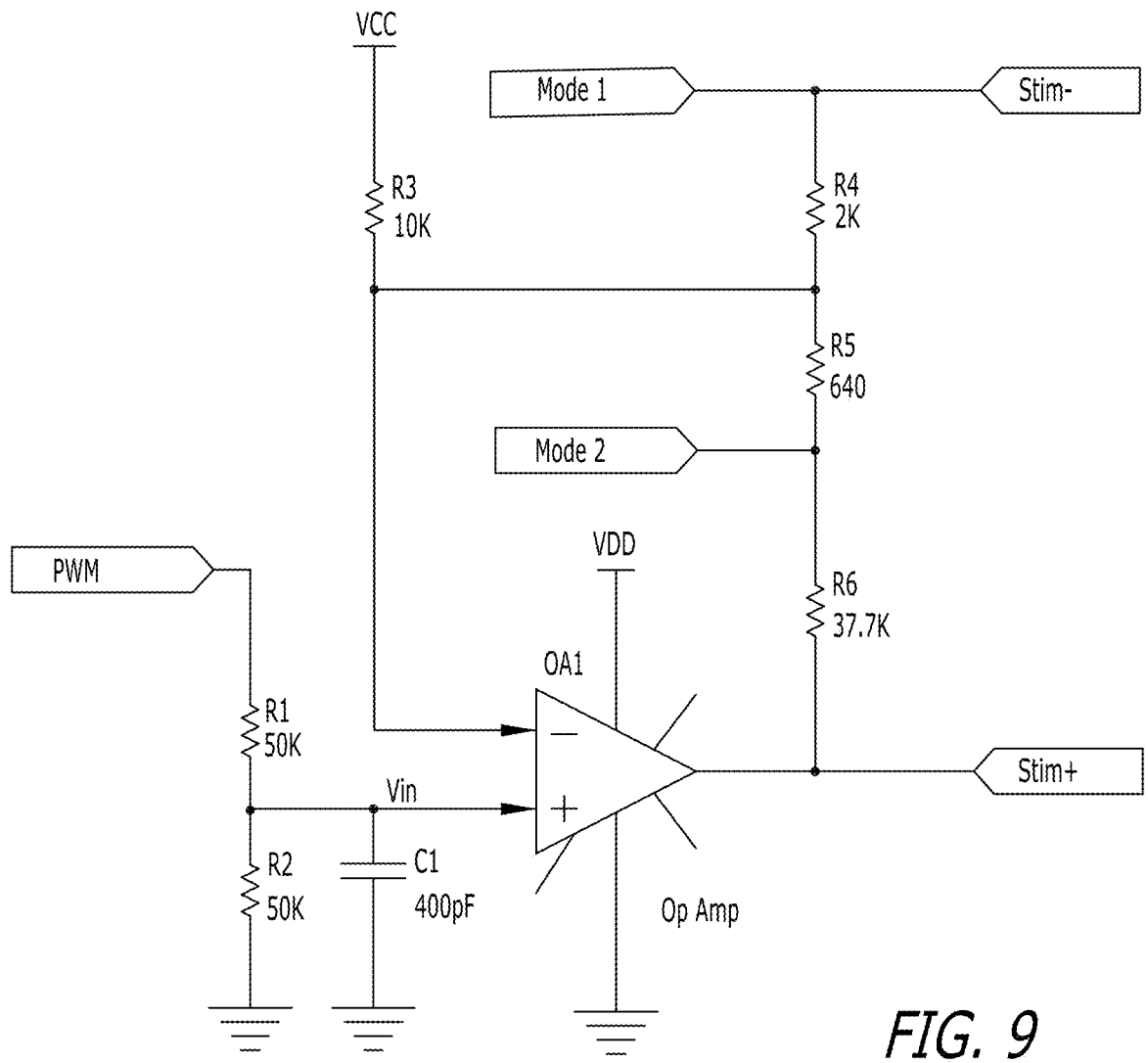
FIG. 9 shows a diagram of a stimulator, according to an example embodiment of the present disclosure.

FIG. 9 shows a diagram of the example stimulator 512 of FIG. 5, according to an example embodiment of the present disclosure. As discussed above, the example stimulator 512 is configured to receive a Mode1 signal and a Mode2 signal from the controller 514 and accordingly output a constant voltage or constant current via Stim+ and Stim− signal lines. For instance, if the Mode1 signal is set to ground and Mode2 is set to a high impedance, then the stimulator 512 is configured to operate in a constant voltage mode. Alternatively, if the Mode1 signal is set to a high impedance and Mode2 is set to ground, then the stimulator 512 is configured to operate in a constant current mode. The magnitude of the voltage and/or current may be set via a PWM signal from the controller 514.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A neuromodulation system comprising:
   a controller wirelessly communicatively coupled to a host computer;
   a signal generator communicatively coupled to the controller;
   a plurality of electromyography ("EMG") electrodes that are hardwired communicatively coupled to the signal generator via respective EMG wires and connected to a mammal at a first location; and
   a microelectrode array comprising electrically conductive contacts, the microelectrode array communicatively coupled to the signal generator and physically connected to the mammal at a second, different location,
   wherein the controller is configured to select a subset of the electrically conductive contacts of the microelectrode array and a subset of the EMG electrodes for delivering a stimulation to the mammal,
   wherein the controller, in conjunction with the signal generator, the selected subset of the plurality of the EMG electrodes, and selected subset of the electrically conductive contacts of the microelectrode array are configured to deliver the stimulation to the mammal based on an instruction received from the host computer, the stimulation being configured to induce or enable voluntary movement or restore function of the mammal, and
   wherein the controller is configured to select either at least some of the plurality of EMG electrodes that are not included in the selected subset of the EMG electrodes or at least some of the electrically conductive contacts of the microelectrode array that are not included in the selected subset of the electrically conductive contacts of the microelectrode array for recording a response from the stimulation.

2. The neuromodulation system of claim 1, further comprising a multiplexer circuit configured to enable the controller to select a first pair of the electrically conductive contacts, as the selected subset, of the microelectrode array and a first pair of the EMG electrodes, as the selected subset, to deliver the stimulation.

3. The neuromodulation system of claim 2, wherein the multiplexer circuit is configured to enable the controller to select a second pair of the electrically conductive contacts, which are not included in the selected subset, of the microelectrode array and a second pair of the EMG electrodes, which are not included in the selected subset of the EMG electrodes, to sense an electrical signal within the mammal.

4. The neuromodulation system of claim 1, wherein the mammal is a human.

5. The neuromodulation system of claim 1, further comprising a wireless power receiver configured to:
   receive power wirelessly from a wireless power supply; and
   rectify the received power into at least one DC voltage for the controller and the signal generator.

6. The neuromodulation system of claim 1, wherein the voluntary movement is of a foot, a toe, an ankle, a knee, a leg, a hip, a shoulder, an arm, a hand, a wrist, a finger, a waist, a trunk, a neck, a head or a combination thereof and the voluntary movement comprises at least one of standing, stepping, a walking motor pattern, sitting down, sitting up, laying down, reaching, grasping, pulling and pushing, swallowing and chewing, breathing, and coughing.

7. The neuromodulation system of claim 1, wherein the stimulation is applied over a cervical portion of the spinal cord or the brainstem.

8. The neuromodulation system of claim 1, wherein the delivered stimulation is applied epidurally over at least one of a lumbar portion, a lumbosacral portion, and a sacral portion of the spinal cord.

9. The neuromodulation system of claim 1, wherein the delivered stimulation is applied to a thoracic or thoracic-lumbar portion of the spinal cord.

10. A method of inducing or enabling a voluntary movement in a mammal with a spinal injury, the method comprising:
receiving in a controller from a wirelessly communicatively coupled host computer an instruction to apply a stimulation to a mammal;
selecting, via the controller, a subset of electrically conductive contacts of a microelectrode array and a subset of electromyography ("EMG") wired or wireless electrodes for delivering the stimulation to the mammal;
instructing a signal generator via the controller to apply the stimulation;
applying via the signal generator the stimulation to the mammal via the selected subset of EMG wired or wireless electrodes that are connected to a first location of the mammal and the selected subset of the electrically conductive contacts of the microelectrode array that are connected to a second location of the mammal; and
selecting, via the controller, either at least some of the plurality of EMG wired or wireless electrodes that are not included in the selected subset of the EMG wired or wireless electrodes or at least some of the electrically conductive contacts of the microelectrode array that are not included in the selected subset of the electrically conductive contacts of the microelectrode array for recording a response from the stimulation.

11. The method of claim 10, further comprising transmitting a control instruction from the controller to a multiplexer circuit to select the subset of the EMG wired or wireless electrodes and the subset of the electrically conductive contacts of the microelectrode array for applying the stimulation.

12. The method of claim 11, wherein selecting the electrically conductive contacts includes selecting a pair of contacts within the microelectrode array.

13. The method of claim 12, further comprising transmitting a control instruction from the controller to a multiplexer circuit to select the at least one of the plurality of EMG wired or wireless electrodes, which are not included in the selected subset of the EMG wired or wireless electrodes, and the at least some of the electrically conductive contacts of the microelectrode array, which are not included in the selected subset, to sense an electrical signal within the mammal.

14. The method of claim 13, further comprising recording movement of the mammal using a sensor,
wherein the sensor includes at least one of a pressure sensor, a temperature sensor, a chemical sensor, a light sensor, a photonic sensor, an acoustic sensor, a flow sensor, a flex sensor, a gyroscope, and an accelerometer.

15. The method of claim 10, further comprising:
receiving power wirelessly in a wireless power receiver from a wireless power supply; and
rectifying the received power in a DC voltage for the controller and the signal generator.

16. The method of claim 15, further comprising:
determining in the controller that received power is insufficient for the stimulation; and
transmitting a message to the wireless power receiver for additional power.

17. A neuromodulation system comprising:
a controller configured to wirelessly receive operating instructions from a host computer;
a signal generator communicatively coupled to the controller;
a multiplexer circuit communicatively coupled to the controller and the signal generator;
a wireless power receiver electrically coupled to a wireless power supply and configured to power the controller, the signal generator, and the multiplexer circuit;
a plurality of EMG wired or wireless electrodes electrically coupled to the multiplexer circuit and configured to deliver a stimulation to a first location of a mammal; and
a microelectrode array including one or more 9×3 arrays of electrodes electrically coupled to the multiplexer circuit and configured to deliver a stimulation to a second location of a mammal,
wherein the controller is configured to select a subset of the electrodes of the microelectrode array and a subset of the EMG wired or wireless electrodes for delivering the stimulation to the mammal,
wherein the controller, in conjunction with the signal generator, the multiplexer circuit, the selected subset of the EMG wired or wireless electrodes, and the selected subset of the electrodes of the microelectrode array are configured to deliver the stimulation to the mammal at the first and second locations, the stimulation being configured to induce or enable voluntary movement or enable restoration of function in the mammal, and
wherein the controller in conjunction with the multiplexer circuit are configured to select either at least some of the plurality of EMG wired or wireless electrodes that are not included in the selected subset of the EMG wired or wireless electrodes or at least some of the electrodes of the microelectrode array that are not included in the selected subset of the electrodes of the microelectrode array for recording a response from the stimulation.

18. The neuromodulation system of claim 17, wherein the stimulation includes an epidural stimulation.

19. The neuromodulation system of claim 17, wherein the multiplexer circuit is configured to enable a pair of the EMG wired or wireless electrodes, as the selected subset, and a pair of the electrodes within the microelectrode array, as the selected subset, to receive the stimulation from the signal generator.

20. The neuromodulation system of claim 17, wherein the controller is configured to transmit a control instruction to the multiplexer circuit to select the at least one of the plurality of EMG wired or wireless electrodes, which are not included in the selected subset of the EMG wired or wireless electrodes, and at least one of the electrodes, which are not included in the selected subset, of the microelectrode array to sense an electrical signal within the mammal.

* * * * *